US006858777B2

(12) United States Patent
Zhong et al.

(10) Patent No.: US 6,858,777 B2
(45) Date of Patent: Feb. 22, 2005

(54) METHODS FOR STABLE TRANSFORMATION OF PLANTS

(75) Inventors: Heng Zhong, Chapel Hill, NC (US); Eric Boudreau, Durham, NC (US); Sabrina Rouse, Clayton, NC (US); Erik Dunder, Hillsborough, NC (US); Weining Gu, Chapel Hill, NC (US); Yin-Fu Chang, Carrboro, NC (US)

(73) Assignee: Syngenta Participations AG, Basel (CH)

( * ) Notice: Subject to any disclaimer, the term of this patent is extended or adjusted under 35 U.S.C. 154(b) by 28 days.

(21) Appl. No.: 09/928,614

(22) Filed: Aug. 13, 2001

(65) Prior Publication Data

US 2002/0073445 A1 Jun. 13, 2002

Related U.S. Application Data

(60) Provisional application No. 60/224,934, filed on Aug. 11, 2000.

(51) Int. Cl.[7] ........................ C12N 15/82; C12N 15/84; A01H 4/00; A01H 5/00
(52) U.S. Cl. ...................... 800/294; 800/293; 800/298; 800/308; 800/309; 800/310; 800/322; 800/278; 435/430; 435/469; 435/470; 435/431
(58) Field of Search ................................. 435/431, 410, 435/430, 468, 469, 470; 800/278, 293, 294, 295, 298, 306, 308, 309, 310, 312, 314, 317.1, 322

(56) References Cited

U.S. PATENT DOCUMENTS

| | | | |
|---|---|---|---|
| 4,940,838 A | 7/1990 | Schilperoort et al. | |
| 4,945,050 A | 7/1990 | Sanford et al. | |
| 5,164,310 A | 11/1992 | Smith et al. | |
| 5,451,513 A | 9/1995 | Maliga et al. | |
| 5,545,817 A | 8/1996 | McBride et al. | |
| 5,545,818 A | 8/1996 | McBride et al. | |
| 5,591,615 A | 1/1997 | Oester et al. | |
| 5,591,616 A | 1/1997 | Hiei et al. | |
| 5,767,368 A | 6/1998 | Zhong et al. | |
| 5,767,373 A | 6/1998 | Ward et al. | |
| 5,767,378 A | 6/1998 | Bojsen et al. | |
| 5,777,200 A | 7/1998 | Ryals et al. | |
| 5,834,292 A | * 11/1998 | Rangan | 435/240.49 |
| 5,939,602 A | 8/1999 | Volrath et al. | |
| 5,994,629 A | 11/1999 | Bojsen et al. | |
| 6,023,012 A | 2/2000 | Volrath et al. | |
| 6,084,155 A | 7/2000 | Volrath et al. | |
| 6,114,603 A | 9/2000 | Christou et al. | 800/293 |
| 6,140,555 A | 10/2000 | Reichert et al. | |
| 6,242,257 B1 | * 6/2001 | Tuli | 435/427 |

FOREIGN PATENT DOCUMENTS

| | | |
|---|---|---|
| EP | 0 301 749 A2 | 2/1989 |
| EP | 0 504869 | 9/1992 |
| EP | 0 604 662 | 6/1994 |
| EP | 0 723 393 B1 | 7/1996 |
| JP | 4-222527 | 12/2002 |
| WO | WO 91/13159 | 9/1991 |
| WO | WO 95/16783 | 6/1995 |
| WO | WO 95/34659 | 12/1995 |
| WO | WO 99/05265 | 2/1999 |
| WO | WO 99/15003 | 4/1999 |
| WO | WO 00/20612 | 4/2000 |

OTHER PUBLICATIONS

Taylor N. et al. DNA and Cell Biology, Nov. 12, 2002.*
Bordas M. et al. Transgenic Research, 1997; vol. 6, No. 1, pp. 41–50.*
Dodds J. et al. Experiments in Plant Tissue Culture; Cambridge University Press, 1982; pp. 98–106.*
Gelvin S. et al., The Plant Cell, Mar. 1997, vol. 9; pp. 317–333.*
Han et al. Can. J. For. Res. 27: 464–470, 1997).*
Chateau S. et al. J. of Experimental Botany, Dec. 2000; vol. 51, No. 353; pp. 1961–1968.*
Jefferson R. EMBO Journal, 1987, vol. 6, No. 13, pp. 3901–3907.*
An, et al, *New cloning vehicles for transformation of higher plants European Molecular Biology Organization Journal*, vol. 4 (2), (1985) pp. 277–284.
Aragao, F. J. L. and E. L. Rech, *Morphological factors influencing recovery of transgenic bean plants (Phaseolus vulgaris L.) of a Carioca cultivar International Journal of Plant Sciences*, vol. 158(2), (1997), 157–163.
Babu, P., Chawla, H.S., *In vitro regeneration and Agrobacterium mediated transformation in gladiolus Journal of Horticultural Science & Biotechnology*, vol. 75(4), (2000) pp. 400–404.
Barwale et al., *Screening of Glycine max and Glycine soja genotypes for multiple shoot formation at the cotyledonary node Theoretical and Applied Genetics*, vol. 72 (1986), pp. 423–428.
Chee et al, *Transformation of soybean (Glycine max) by infecting germinating seeds with Agrobacterium tumefaciens Plant Physiology*, vol. 91 (1989), pp. 1212–1218.
Chilton, M–D, *Agrobacterium gene transfer: progress on a "poor man's vector" for maize Proceedings of the National Academy of Sciences, USA*, vol. 90(8), (Apr. 15, 1993) pp. 3119–3120.

(List continued on next page.)

*Primary Examiner*—David T. Fox
*Assistant Examiner*—Russell Kallis
(74) *Attorney, Agent, or Firm*—Syngenta Participations AG

(57) ABSTRACT

Multiple shoot structures are induced from plant tissues (e.g., shoot apices or axillary buds on an artificial medium) to produce multiple shoot cultures. These multi-shoot cultures are then transformed by known transformation methods. Plants are subsequently regenerated from the transformed cells. Crops that may be efficiently transformed by this method include plants normally recalcitrant to transformation such as sugar beet, sunflower, soybean, cotton, tobacco, tomato, peanuts, melons, watermelon, squash, *Brassica*, and pepper.

17 Claims, No Drawings

OTHER PUBLICATIONS

Christou, P., *Genetic transformation of crop plants using microprojectile bombardment Plant Journal*, vol. 2(3), (1992) pp. 275–281.

Crossway et al, *Integration of foreign DNA following microinjection of tobacco mesophyll protoplasts Molecular Genetics and Genomics*, vol. 202 (1986), pp. 179–185.

D'Halluin et al., *Transformation of sugarbeet(Beta vulgaris L.) and evaluation of herbicide resistance in transgenic plants Bio/Technology*, vol. 10 (1992), pp. 309–314.

Elliot et al. "Regeneration of Normal and Transformed Sugar Beet: The Role of $N^6$–Benzyladenine." in: eds. Kaminek et al., *Proceedings of the International Symposium on Physiology and Biochemistry of Cytokinins in Plants*, (SPB Publishing, The Hague, 1992), pp. 329–334.

Fromm et al, *Expression of genes transferred into monocot and dicot plant cells by electroporation Proceedings of the National Academy of Sciences*, US, vol. 82 (Sep., 1985), pp. 5824–5828.

Fry et al., "Genotype–Independent Transformation of Sugarbeet Using Agrobacterium Tumefaciens" Abstract # 384 in *Molecular Biology of Plant Growth and Development, Third International Congress of the International Society for Plant Molecular Biology* (R. B. Hallick, editor, Tucson, Arizona, USA 1991).

Goldschmidt–Clermont, M., *Transgenic expression of aminoglycoside adenine transferase in the chloroplast: a selectable marker for site–directed transformation of Chlamydomonas Nucleic Acids Research*, vol. 19 (1991), pp. 4083–4089.

Gonsalves et al., *Somatic embryogenesis and regeneration from cotyledon explants of six squash cultivars HortScience*, vol. 30, (1995) 1295–1297.

Haldrup, et al., *The xylose isomerase gene from Thermoanaerobacterium thermosulfurogenes allows effective selection of transgenic plant cells using D–xylose as the selection agent Plant Molecular Biology*, vol. 37 (1998), p. 287–296.

Hall et al, *A high efficiency technique for the generation of transgenic sugar beets from stomatal guard cells Nature Biotechnology*, vol. 14 (Sep., 1996) pp. 1133–1138.

Hall et al,.*Computer–Assisted Identification of Protoplasts Responsible for Rave Division Events Reveals Guard–Cell Totipotency Plant Physiology*, vol. 107(4) (1995), pp. 1379–1386.

Harms et. al, *Clonal Propagation in vitro of red beet (Beta vulgaris ssp.) by Multiple Adventitious Shoot Formation Plant Cell Tissue Organ Culture 2*, 93–102 (1983).

Herrera–Estrella et al, *Expression of chimaeric genes transfered into plant cells using a Ti–plasmid–derived vector Nature*, vol. 303 (May 19, 1983), pp. 209–213.

Herrera–Estrella et al., *Chimeric genes as dominant selectable markers in plant cells European Molecular Biology Organization Journal*, vol. 2(6) (1983), pp. 987–995.

Herrera–Estrella et al., "*Agrobacterium* as a vector system for the introduction of genes into plants," in: Ed. Dodds, John H., *Plant Genetic Engineering* (New York, Cambridge University Press, 1985), pp. 61–93.

Hood et al, *The hypervirulence of Agrobacterium tumefaciens A281 is encoded in a region of pTIBoS42 outside of T–DNA Journal of Bacteriology*, vol. 168 (1986), pp. 1291–1301.

Hood et al,.*Restriction endonuclease map of p TiBoS42, a potential Ti–plasmid vector for genetic engineering of plants Bio/Technology*, vol. 2 (Aug., 1984), pp. 702–709.

Hooykaas et al, *Transformation of Plant Cells via Agrobacterium Plant Molecular Biology*, vol. 13, (1989), pp. 327–336.

Horch et al, *Inheritance of Functional Foreign Genes in Plants Science*, vol. 223, (1984) pp. 496.

Ishida et al, *High efficiency transformation of maize (Zea mays L) mediated by Agrobacterium tumefaciens Nature Biotechnology*, vol. 14:7 (Jun., 1996), pp. 745–750.

Jefferson et al, *β–Glucuronidase from Escherichia coli as a Gene Fusion Marker Proceedings of the National Academy of Sciences*, US, vol. 83 (Nov., 1986), pp. 8447–8451.

Jefferson, R.A., *Assaying Chimeric Genes in Plants: The GUS Gene Fusion System Plant Molecular Biology Reporter* vol. 5(4), (1987) pp. 387–405.

Jin et al, *Genes responsible for the supervirulence phenotype of Agrobacterium tumefaciens A281* Journal of Bacteriology, vol. 169 (1987), pp. 4417–4425.

Komari et al, *Transformation of cultural cells of Chenopodium quinoa by binary vectors that carry a fragment of DNA from the virulent region of p TiBo 542 Plant Cell Reports*, vol. 9, (1990) pp. 303–306.

Komari et al. *Physical and functional map of supervirulent Agrobacterium tumefaciens tumor–inducing plasmid p TiBo542* Journal of Bacteriology, vol. 166(1) (Apr. 1986) pp. 88–94.

Komari et al., *Vectors carrying two separate T–DNAs for co–transformation of higher plants mediated by Agrobacterium tumefaciens and segregation of transformants free from selection markers The Plant Journal*, vol. 10(1) (Jul. 1996), pp. 165–174.

Komari, T., *Transformation of callus cultures of nine plant species mediated by Agrobacterium Plant Science*, vol. 60(2) (1989), pp. 223–229.

Kotowska et al., *Preliminary Report on Epidermis Culture of Sugar Beet Bulletin of the Polish Academy of Sciences*, vol. 32, 11–12 (1984).

Kotowska, *Morphogenetical capacities of inflorescence shoot tissues of sugar beet in in vitro cultures: II. Division and differentiation of mature tissues cells Beitraege–zur–Biologie–der–Pflanzen*, vol. 67 (2) (1992 (1993)), pp. 209–223 [Summary in English].

Krens et al., *The effect of exogenously–applied phytohormones on gene transfer efficiency in sugarbeet (Beta vulgaris L.) Plant Science*, vol. 116, (1996) pp. 97–106.

Kubo et al, *Nucleotide sequence of the chloroplast rrn 16–trnV–rps12–ndhB in sugar beet* GenBank Accession No. AB032426 [online], [retrieved on Sep. 25, 2002]. Retrieved from the Internet:<URL:http://www.ncbi.nlm.nih.gov/entrez/>.

Lindsey, K. and Gallois, P., *Transformation of Sugarbeet (Beta vulgaris) by Agrobacterium tumefaciens Journal of Experimental Botany*, vol. 41(226) (1990), pp. 529–536.

Lindsey et.al, "Transformation in Sugar Beet (*Beta vulgaris L.*)," in *Biotechnology in Agriculture and Forestry*, vol. 23, *Plant Protoplasts and Genetic Engineering IV* (Y. P. S. Bajaj, Ed., Springer–Verlag, Berlin, 1993) pp. 147–169.

McBride et al, *Controlled expression of plastid transgenes in plants based on a nuclear DNA–encoded and plastid–targeted T7 RNA polymerase Proceedings of the National Academy of Sciences*, US, vol. 91 (Jul. 19, 1994), pp. 7301–7305.

McCabe et al, *Stable transformation of soybean (Glycine max) by Particle Acceleration Bio/Technology*, vol. 6, (Aug., 1988), pp. 923–926.

Moloney et al., *Transformation and Foreign Gene Expression Monographs on the Theoretical and Applied Genetics*, vol. 19, (1993) pp. 148–167.

Ni et al, *Strength and tissue specificity of chimeric promoters derived from the octopine and mannopine synthase genes Plant Journal*, vol. 7(4) (1995), pp. 661–676.

Norris et al, *The intron of Arabidopsis thaliana polyubiquitin genes is conserved in location and is a quantitative determinant of chimeric gene expression Plant Molecular Biology*, vol. 21(5) (1993), pp. 895–906.

Paszkowski et al, *Direct Gene Transfer to Plants* European Molecular Biology Organization Journal, vol. 3(12), (1984), pp. 2717–2722.

Reed et al., *Phosphomannose Isomerase: An efficient selectable marker for plant transformation In Vitro Cellular and Developmental Biology—Plant*, vol. 37 (Mar.–Apr. 2001) pp. 127–132.

Sander, *Transformation von Beta vulgaris L.*, (Ph.D. Thesis, University of Hannover, Germany 1994).

Schneider et al., *Adventitious Shoot Formation in a Tissue Culture Line of Sugarbeet Biochem. Physiol. Pflanzen.* 182, 485–490 (1987).

Sévenier et al, *High level fructan accumulation in a transgenic sugar beet Nature Biotechnology* 16, (Sep., 1998), pp. 843–846.

Smith, R.H. and Hood, E.E., *Agrobacterium tumefaciens Transformation of Monocotyledons Crop Science* 35(2), (Mar.–Apr., 1995), pp. 301–309.

Staub, J.M. and Maliga, P., *Long regions of homologous DNA are incorporated into the tobacco plastid genome by transformation The Plant Cell*, vol. 4 (Jan., 1992), pp. 39–45.

Svab et al, *High–frequency plastid transformation in tobacco by selection for a chimeric aadA gene Proceedings of the National Academy of Sciences, US*, vol. 90(3) (Feb. 1993), pp. 913–917.

Svab et al, *Stable transformation of plastids in higher plants Proceedings of the National Academy of Sciences, US*, vol. 87(21) (Nov. 1990), pp. 8526–8530.

Tricoli et al, *Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus Bio/technology*, vol. 13 (Dec., 1995), pp. 1458–1465.

Vancanneyt et al, *Construction of an intron–containing marker gene: Splicing of the intron in transgenic plants and its use in monitoring early events in Agrobacterium–mediated plant transformation Molecular and General Genetics*, vol. 220(2) (Jan. 1990) pp. 245–250.

Zhang et al., *Genetic transformation of commercial cultivars of oat (Avena sativa L.) and barley (Hordeum vulgare L.) using in vitro shoot meristematic cultures derived from germinated seedlings Plant Cell Reports*, vol. 18, (1999), pp. 959–966.

Zhong et al., *The Competence of Maize Shoot Meristems for Integrative Transformation and Inherited Expression of Transgenes Plant Physiology*, vol. 110, (1996), pp. 1097–1107.

ATCC Accession No. 37394 [online], [retrieved on Sep. 26, 2001], Retrieved from the Internet: <URL:http://www.atcc.org/SearchCatalogs/>.

Detrez et al.*Direct Organogenesis from Petiole and Thin Cell Layer Explants in Sugar Beet Cultured in Vitro Journal of Experimental Botany*, vol. 39, No. 204, (Jul. 1988) pp. 917–926.

Joersbo et al., *Analysis of mannose selection used for transformation of sugar beet Molecular Breeding*, vol. 4 (1998), pp. 111–117.

Ritchie et al., *In Vitro Shoot Regeneration from Callus, Leaf Axils and Petioles of Sugar Beet (Beta vulgaris L.) Journal of Experimental Botany*, vol. 40, No. 211 (Feb. 1989), pp. 277–283.

Snyder et al., *Introduction of pathogen defense genes and a cytokinin biosynthesis gene into sugarbeet (Beta vulgaris L.) by Agrobacterium or particle bombardment Plant Cell Reports*, vol. 18 (1999), pp. 829–834.

ATCC Accession No. 53487 [online catalog detail], [retrieved on Oct. 3, 2002]. Retrieved from the Internet: <URL: http://www.atcc.org/SearchCatalogs/.

Snyder et al, *Genetic transformation of sugarbeet using particle bombardment and novel plant pathogen defense genes* 29th *Biennial Meeting of American Society of Sugar Beet Technologists*, Phoenix, AZ (1997) pp. 48.

\* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence -continued

```
<220> FEATURE:
<223> OTHER INFORMATION: Description of Artificial Sequence:
      oligonucleotide

<400> SEQUENCE: 1
ttcttacgcg ttactcaccc g                                              21

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
aaactgcaga aagaagtccc ggctccaagt                                     30

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
aaaggatcca aattgacggg ttagtgtg                                       28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
aaactgcagt cgcactatta cggatacgaa                                     30
```

METHODS FOR STABLE TRANSFORMATION OF PLANTS

RELATED APPLICATIONS

The present application claims the benefit of U.S. Provisional Application Serial No. 60/224,934, filed Aug. 11, 2000, the disclosure of which is incorporated herein in its entirety.

FIELD OF THE INVENTION

The present invention relates to the transformation and regeneration of transformed plants. In particular, the invention relates to the transformation of plants normally recalcitrant to transformation.

BACKGROUND OF THE INVENTION

Improvement of plant varieties through genetic transformation has become increasingly important for modern plant breeding. Genes of potential commercial interest, such as genes conferring to a plant traits of disease resistance, insect resistance or improved quality, may be incorporated into crop species through various gene transfer technologies.

The development of an efficient transformation system is necessary for the analysis of gene expression in plants. The requirements for such a system include a proper target plant tissue that will allow efficient plant regeneration, a gene delivery vehicle that delivers foreign DNA efficiently into the target plant cells, and an effective method for selecting transformed cells. In genetic transformation of dicotyledonous species, for example, transformation systems utilizing the bacterium *Agrobacterium tumefaciens* have been frequently used as vehicles for gene delivery. The preferred target tissues for *Agrobacterium*-mediated transformation presently include cotyledons, leaf tissues, and hypocotyls. High velocity microprojectile bombardment offers an alternative method for gene delivery into plants.

Although genetic transformation and subsequent regeneration is largely a matter of routine nowadays for many plants species, several commercially significant crops such as sugar beet, squash, sunflower, soybean, and cotton have remained recalcitrant to transformation by most of the numerous methods that are available.

*Beta vulgaris* (which includes sugar beet, fodder beet, table beet and Swiss chard) is one example where, despite transient expression in some cells and occasional success with specific genotypes, no simple routine method is available for the production of transgenic plants. The recalcitrance to transformation of sugar beet protoplasts is well-documented. See, for example, International Patent Application No. WO 91/13159 and K. D'Halluin et. al., *Bio/Technology*, 10 309–314 (1992)). Regarding *Agrobacterium*-mediated gene transfer, "the sugarbeet's recalcitrance is renowned," and "most of the techniques reported for the production of transgenic sugarbeet plants require the expert skill of laboratories that developed them and [has] proved not easily reproducible by others." F. A. Krens et al., *Plant Sci.* 116, 97–106 (1996), citing M. C. Elliot et al., in *Physiology and Biochemistry of Cytokinins in Plants*, pages 329–334 (SPB Publishing, The Hague, 1992); K. Lindsey et al., *J. Exp. Bot.* 41, 529–536 (1990); and D'Halluin et al., supra. The Krens et al. paper states further that "the method of choice . . . is one using cotyledons as the explant system, which has only been described superficially." Krens et al., supra, citing J. E. Fry et al., Abstract # 384 in *Molecular Biology of Plant Growth and Development, Third International Congress of the International Society for Plant Molecular Biology* (R. B. Hallick, editor, Tuscon, Ariz., USA 1991). However, even this method is not highly efficient; as an example, one researcher reported obtaining only 21 transgenic shoots, including several chimeras, from 15,000 inoculated explants. U. Sander, *Transformation von Beta vulgaris L.*, (Ph.D. Thesis, University of Hanover, Germany 1994). The Krens et al. paper itself reports a 0.9% transformation frequency in sugarbeets using a cotyledonary node and kanamycin selection technique. Krens et al., supra, at page 103.

There are brief descriptions in the literature relating to callus production from the epidermal cells of sugar beet (see Kotowska et al., *Bull. of the Polish Acad. Sci.* 32, 11–12 (1984); Kotowska, *Beitr. Biol. Pflanz.* 67, 209–223 (1992)), and several reports describing adventitious bud production on the epidermis of sugar beet petioles. See e.g., Harms et. al., *Plant Cell Tissue Organ Culture* 2, 93–102 (1983); Schneider et al., *Biochem. Physiol. Pflanz.* 182, 485–490 (1987)). However, these reports present no evidence that transformed sugar beet plants can be regenerated using these methods.

Sugarbeet transformation using sugarbeet protoplasts (through stomata guard cells) has been reported. See, e.g., R. Hall et al., *Nature Biotechnology* 14, 1133–1138 (1996); R. Hall et al., *Plant Physiol.* 107, 1379–1386 (1995); R. Sevenier et al., *Nature Biotechnology* 16, 843–846 (1998); and European Patent EP 0 723 393 B1. However, protoplasts isolated from sugar beet leaves vary in size and morphology, reflecting the high degree of cellular heterogeneity present within the source tissue at both physiological and cytogenetic levels. Accordingly, transformation techniques utilizing protoplasts requires the expert skill of laboratories that have developed particular methods, and the results are not easily reproducible.

At best, transformation techniques for sugarbeets have heretofore been very dependent on explant source, plant genotype and selection conditions used, and high efficiencies of transformation have been very difficult to achieve. See, e.g., K. Lindsey et al., *J. Experimental Botany* 41, 529–536 (1990); K. Lindsey et. al, "Transformation in Sugar Beet (*Beta vulgaris L.*)," in *Biotechnology in Agriculture and Forestry*, Vol. 23, *Plant Protoplasts and Genetic Engineering IV* (Y. P. S. Bajaj, Ed., Springer-Verlag, Berlin, 1993). Sugar beet is an important crop in the temperate climate region. Over 30% of the world's sugar consumption comes from sugar beet. There is thus a continuing need for a simple, high efficiency transformation method which may be applicable to beet and other plants that have heretofore been recalcitrant to transformation.

Other plants recalcitrant to transformation for which simple, high efficiency transformation methods are needed include the various species of squash. In one study, summer squash cultivars were regenerated via somatic embryogenesis using cotyledons excised from seeds. C. Gonsalves, *HortScience* 30, 1295–1297 (1995). However, the regeneration efficiency of this method was calculated as 0.3 plantlets per initial explant. Id. In other reports, the production of transgenic squash is reported, but the transformation procedures used to obtain the regenerated plants are not described or publicly available. See, e.g., D. Tricoli et al., *Bio/Technology* 13, 1458–1465, 1464 (1995).

Transformation methods using seedling (non-excised) shoot tips or excised shoot tips have been described. See U.S. Pat. No. 5,164,310 to Smith et al. (incorporated herein by reference in its entirety); P. Chee et al., *Plant Physiol.* 91, 1212–1218 (1989); F. J. L. Aragao et al., *Int. J. Plant Sci.* 158, 157–163 (1997); and P. Christou et al., *Plant J.* 8, 275–281 (1992). In these methods, shoot tips either remained attached to seedlings or germinating seeds at the time of transformation, or were excised from seedlings. In the latter case, only one shoot per excised shoot tip was ultimately produced.

Transformation methods using shoot tip-derived meristematic cultures have also been described. See, e.g., U.S. Pat. No. 5,767,368 to Zhong et al. (incorporated herein by reference in its entirety); H. Zhong et al., *Plant Physiol.* 110, 1097–1107 (1996); and S. Zhang et al., *Plant Cell Reports* 18, 959–966 (1999). However, these methods have been shown to be effective in only a handful of monocotyledonous plants (i.e., corn, barley and oat), and no transformed dicot plants have been successfully regenerated following transformation attempts using those methods. Furthermore, transformation of monocots using shoot-tip derived meristematic cultures, as described in the above references, was generally achieved by microprojectile bombardment (i.e., generally not mediated by *Agrobacterium tumefaciens*).

SUMMARY OF THE INVENTION

The present inventors have discovered a method by which multiple shoot structures are induced from plant tissues (e.g., shoot apices or axillary buds on an artificial medium) to produce multiple shoot cultures. These multi-shoot cultures are then transformed with *Agrobacterium tumefaciens*, high velocity bombardment with DNA-coated microprojectiles, or other known transformation methods. After transformation, the multiple shoot cultures may be transferred to a selection medium to differentiate transformed and non-transformed cells. Plants are subsequently regenerated from the transformed cells upon transfer to a regeneration medium and/or a rooting medium. The present invention may be applied to commercial crops that include sugar beet, sunflower, soybean, cotton, peanuts, melons, watermelon, squash, *Brassica*, tobacco, tomato and pepper. The present invention provides certain advantages over existing methods because it can be used to transform plants that are normally recalcitrant to transformation at high efficiencies. The present invention invention is also used to transform the plastid genome of plants, in particular of dicotyledonous plants.

The present invention provides a method of producing a transformed dicotyledonous plant, comprising: (a) culturing a tissue of a dicotyledonous plant recalcitrant for transformation on a culture medium to produce a multiple shoot culture from the tissue; (b) introducing a nucleic acid into a cell of the multiple shoot culture, thereby producing a transformed cell comprising the nucleic acid; and (c) regenerating a transformed plant from the transformed cell. The tissue is preferably a meristematic tissue, preferably excised from a shoot apex, an axillary bud or a floral meristem, or the tissue is callus tissue. In a preferred embodiment, the plant is a member of the Cucurbitaceae family or the Chenopodiacea family. In another preferred embodiment, the plant is selected from the group consisting of sugar beet, sunflower, soybean, cotton, melons, watermelon, and squash. Preferably, the plant is sugar beet, squash, melon or watermelon. In another preferred embodiment, the tissue is excised from the shoot tip of a seedling of the plant. In another preferred embodiment, the culture medium comprises at least one plant growth regulator, preferably a cytokinin. In another preferred embodiment, the growth regulator is selected from the group consisting of 6-furfurylaminopurine (kinetin), 6-benzyl-aminopurine (6-BAP), 6-dimethyallylamino-purine (2ip), trans-6-(4-hydroxzy-3-methlbut-2-enyl)amino-urine (zeatin), TDZ, gibberellic acid (GA), IAA, NAA, dicamba, 2,3,5-T and 2,4-D. The concentration of growth regulator in the culture medium is preferably between about 0.01 mg/L to about 25 mg/L, more preferably between about 0.01 mg/L to about 10 mg/L, more preferably between about 0.01 mg/L to about 5 mg/L, more preferably between about 0.05 mg/L to about 8 mg/L. In another preferred embodiment, the nucleic acid is introduced into the cell by microparticle bombardment, electrophoresis or electroporation, or using a bacterium belonging to the genus *Agrobacterium*. In another preferred embodiment, the nucleic acid comprises a nucleic acid that is heterologous to the dicotyledonous plant. Preferably, the nucleic acid comprises a gene that encodes a polypeptide having PPO activity, a gene that encodes a polypeptide having phosphomannose isomerase (PMI) activity, a gene that encodes a polypeptide having xylose isomerase (xylA) activity or a gene that encodes a polypeptide having GUS activity. Preferably, the nucleic acid is a vector comprising a nucleic acid comprising a gene heterologous to the plant.

In yet another preferred embodiment, step (c) of the method comprises: selecting a multiple shoot culture comprising a transformed cell; growing the multiple shoot culture under conditions that promote shoot elongation to produce at least one transformed shoot; and then growing the at least one transformed shoot into a mature transformed plant. Preferably, the at least one transformed shoot grows into a mature transformed plant after growing the at least one transformed shoot on a medium that promotes root formation.

In yet another preferred embodiment, step (c) of the method comprises: selecting a multiple shoot culture comprising a transformed cell; growing the multiple shoot culture under conditions that promote shoot elongation to produce at least one transformed shoot; cloning the at least one transformed shoot; and allowing the cloned shoot to mature into a transformed plant. Preferably, the cloned shoot grows into a mature transformed plant after growing the cloned shoot on a medium that promotes root formation.

The present invention further provides a transformed plant cell produced by any one of the methods above; a multiple shoot culture produced by any one of the methods above; a transformed plant produced by any one of the methods above. In a preferred embodiment, the transformed plant is a squash plant, a melon plant or a watermelon plant that expresses a polypeptide having PMI activity. In another preferred embodiment, the transformed plant is a sugar beet plant that expresses a polypeptide having PPO activity.

The present invention further provides a seed produced by a transformed plant above, wherein the seed comprises the nucleic acid transformed into the multiple shoot culture and a plant grown from the seed.

The present invention further provides a method of producing a plant comprising a transformed plastid genome, comprising: (a) culturing a tissue of a plant on a culture medium to produce a multiple shoot culture from the tissue; (b) introducing a nucleic acid into a plastid genome of a cell of the multiple shoot culture, thereby producing a transformed plastid genome of said cell comprising the nucleic acid; and (c) regenerating a transformed plant from the transformed cell. In a preferred embodiment, the tissue is meristematic tissue, preferably is excised from a shoot apex, an axillary bud, a floral meristem or leaf tissue, or the tissue is callus tissue. In a preferred embodiment, the transformed cell is homoplasmic for transformed plastid genomes. In another preferred embodiment, the plant is homoplasmic for transformed plastid genomes.

In another preferred embodiment, the plant is a dicotyledonous plant. Preferably, the plant is a member of the Cucurbitaceae family or of the Chenopodiacea family. In another preferred embodiment, the plant is selected from the group consisting of sugar beet, sunflower, soybean, cotton, peanuts, melons, watermelon, tobacco, tomato, squash, *Brassica* and pepper. Preferably, the plant is sugar beet, tobacco and tomato. In another preferred embodiment, the tissue is excised or derived from the shoot tip of a seedling of the plant. In another preferred embodiment, the culture medium comprises at least one plant growth regulator, preferably a cytokinin. In another preferred embodiment, the growth regulator is selected from the group consisting of 6-furfurylaminopurine (kinetin), 6-benzyl-aminopurine (6-BAP), 6-dimethyallylamino-purine (2ip), trans-6-(4-hydroxy-3-methlbut-2-enyl)amino-urine (zeatin), TDZ, gibberellic acid (GA), IAA, NAA, dicamba, 2,3,5-T and 2,4-D. Preferably, the concentration of growth regulator in the culture medium is between about 0.01 mg/L to about 25 mg/L, more preferably between about 0.01 mg/L to about 10 mg/L, more preferably between about 0.01 mg/L to about 5 mg/L, more preferably between about 0.05 mg/L to about 8 mg/L. The nucleic acid is preferably introduced into the cell by microparticle bombardment, electrophoresis or electroporation. Preferably, the nucleic acid comprises a nucleic acid that is heterologous to the dicotyledonous plant. Preferably, the nucleic acid is a vector comprising a nucleic acid comprising a gene heterologous to the dicotyledonous plant.

In another preferred embodiment, step (c) of the method comprises: selecting a multiple shoot culture comprising a transformed cell; growing the multiple shoot culture under conditions that promote shoot elongation to produce at least one transformed shoot; and then growing the at least one transformed shoot into a mature transformed plant. In a preferred embodiment, the at least one transformed shoot grows into a mature transformed plant after growing the at least one transformed shoot on a medium that promotes root formation.

In another preferred embodiment, step (c) of the method comprises: selecting a multiple shoot culture comprising a transformed cell; growing the multiple shoot culture under conditions that promote shoot elongation to produce at least one transformed shoot; cloning the at least one transformed shoot; and allowing the cloned shoot to mature into a transformed plant. Preferably, the cloned shoot grows into a mature transformed plant after growing the cloned shoot on a medium that promotes root formation.

The present invention further provides a transformed plastid genome produced by any one of the methods above; a plastid comprising a transformed plastid genome produced by any one of the methods above and a transformed plant cell produced by any one of the methods above. Preferably, the plant cell is homoplasmic for the transformed plastid genome.

The present invention also provides a multiple shoot culture produced by any one of the methods above and a transformed plant produced by any one of the methods above. Preferably, the plant is homoplasmic for the transformed plastid genome.

The present invention further provides a seed produced by a transformed plant above, wherein the seed comprises the nucleic acid transformed into the multiple shoot culture and a plant grown from the seed.

The foregoing and other aspects of the present invention are explained in detail in the specification set forth below.

DETAILED DESCRIPTION OF THE PREFERRED EMBODIMENTS

The present invention will now be described more fully hereinafter with reference to the accompanying specification, in which preferred embodiments of the invention are described. This invention may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Except as otherwise indicated, standard methods may be used for the production of cloned genes, expression cassettes, vectors (e.g., plasmids), proteins and protein fragments, and transformed cells and plants according to the present invention. Except as otherwise indicated, standard methods may be used for the production of cloned genes, expression cassettes, vectors (e.g., plasmids), proteins and protein fragments according to the present invention. Such techniques are known to those skilled in the art. See e.g., J. Sambrook et al., *Molecular Cloning: A Laboratory Manual Second Edition* (Cold Spring Harbor Laboratory, Cold Spring Harbor, N.Y., 1989), and F. M. Ausubel et al., *Current Protocols In Molecular Biology* (Green Publishing Associates, Inc. and Wiley-Interscience, New York, 1991); J. Draper et al., eds., *Plant Genetic Transformation And Gene Expression: A Laboratory Manual,* (Blackwell Scientific Publications, 1988); and S. B. Gelvin & R. A. Schilperoort, eds., *Introduction, Expression, And Analysis Of Gene Production In Plants.*

The methods of the present invention are useful for producing transformed plants. Transformed plants of the present invention are produced by first culturing a plant tissue on a culture medium in order to produce a multiple shoot culture from the tissue. A nucleic acid is then introduced into a cell of the multiple shoot culture, thereby producing a transformed cell comprising the nucleic acid. Finally, a transformed plant from the transformed cell is regenerated.

In a preferred embodiment of the invention, plant cells that are transformed are normally recalcitrant to transformation. In a particularly preferred embodiment, plant cells that are transformed are dicotyledonous plant cells, and most preferably are dicotyledonous plant cells recalcitrant to transformation as defined herein. "Plant cells" or "plants" as used herein includes whole plants, plant cells, or sub-cellular plant organelles (i.e., plastids) in plant tissue, or plant tissue, plant cells, plant cell suspensions, sub-cellular plant organelles and protoplasts in culture. Plant tissue includes differentiated and undifferentiated tissues of plants, including but not limited to, roots, shoots, leaves, pollen, seeds, tumor tissue, gametophytes, sporophytes, microspores and various forms of cells in culture, such as single cells, protoplasts, embryos and callus tissue. The plant tissue may be in a plant, or in an organ, tissue or cell culture.

In general, dicotyledonous plants are flowering plants having an embryo with two cotelydons, leaves with net-like veins, and vascular bundles in the stem in a ring surrounding the central pith. As stated above, dicotyledonous plants that may be transformed by the present invention are preferably those dicotyledonous plants that are recalcitrant to transformation. Generally, a plant recalcitrant to transformation is one whose cells either cannot be transformed by present known transformation methods (i.e., microprojectile bombardment or biolistic transformation, *Agrobacterium*-mediated transformation, electroporation, electrophoresis and the like), or is transformed by such methods at a low transformation efficiency (i.e., lower than 1.0%, or lower than 0.5%, or even lower than 0.1%). Plants recalcitrant to transformation are also those plants whose cells, tissue, protoplasts or calli may be transformed by known methods, but which transformed cells, tissue, protoplasts or calli are unable to regenerate a mature transgenic plant.

In a preferred embodiment of the invention, the dicotyledonous plant is a member of the Cucurbitaceae family. In another preferred embodiment of the invention, the dicotyledonous plant is a member of the Chenopodiacea family. In a more preferred embodiment, the dicotyledonous plant is selected from the group consisting of *Beta vulgaris* (i.e., sugar beet, fodder beet, table beet and Swiss chard), sunflower, soybean, cotton, peanuts, melons, watermelon, squash, tobacco, tomato, *Brassica* and pepper. In a most preferred embodiment, the dicotyledonous plant is sugar beet or squash.

In the present invention, a plant is transformed by first producing a multiple shoot culture from tissue from the plant. As used herein, the term "multiple shoot culture" may be also referred to interchangeably as an "explant." Tissue that may be utilized in the present invention includes but is not limited to meristematic tissue, root tip tissue, shoot tip tissue (including leaf primordia, apical regions, axillary regions, hypocotyl and cotyledonous leaves), seedling shoot apex (which may include meristem, leaf blade, leaf petiole, or blade-petiole transition zone tissue), and callus tissue. In a preferred embodiment, the tissue from which a multiple shoot culture is produced from meristematic tissue excised from a shoot apex, an axillary bud or a floral meristem.

In one embodiment of the invention, a multiple shoot culture may be obtained by first germinating seeds on a seed germination medium, preferably under aseptic culture. Seed germination techniques are known to those skilled in the art. In a preferred embodiment of the invention, the seed germination medium (GM) comprises Murashige and Skoog (MS) salts (commercially available from Sigma Chemicals, St. Louis, Mo.). The GM may further comprise a carbohydrate source such as sucrose, which is preferred. The carbohydrate source may be present in an amount of about 20–40 g/L (about two to four percent w/v), and preferably about 30 g/L (about three percent w/v). Optionally and preferably, the GM may comprise $B_5$ vitamins, myo-inositol (100 mg), pantothenic acid and a plant tissue culture gelling agent such PHYTAGEL™ (also available from Sigma Chemical). Plant growth regulators with cytokinin-like function (described below) may also (and preferably) be added to the seed germination medium. Suitable plant growth regulators with cytokinin-like function include but are not limited to 6-benzyl-aminopurine (6-BAP or BA), 6-furfurylaminopurine (kinetin), 6-imethyallylamino-purine (2-ip), trans-6-(4-hydroxzy-3-methylbut-2-enyl)aminourine (zeatin) and the like. In GM, the plant growth regulator may be added to a concentration as low as about 0.5 mg/L or about 0.1 mg/L, or about 0.05 mg/L, or even lower; alternatively, the plant growth regulator may be added to a concentration of up to about 1.0 mg/L or about 2.0 mg/L, or about 5 mg/L, or even higher. The addition of casein hydrolysate, proline and/or glutamin may also be beneficial. For some dicotyledonous crops such as sugar beet, the addition to the GM of an auxin inhibitor such as 2,3,5-triiodobenzoic acid (TIBA) may be beneficial.

After the seeds have germinated (i.e., become seedlings) on the GM for about 7–14 days, the shoot tips of the seedlings are excised and cultured (i.e., plated) on a culture medium referred to herein as a shoot multiplication medium (SMM). Preferably, the shoot tip comprises both apical and axillary meristem regions, leaf primordia, 3–4 mm of hypocotyl, and the cotyledons, which may be cut back to reduce further elongation. Of course, other plant tissue used in the present invention to produce multiple shoot cultures may also be plated on the SMM. In a preferred embodiment of the invention, the SMM comprises MS salts, a carbohydrate source (preferably sucrose), $B_5$ vitamins and a gelling agent such as PHYTAGEL™. In addition, the SMM contains at least one cytokinin-like growth regulator such as BA, kinetin, 2ip, zeatin and the like. BA is the preferred growth regulator for inducing shoot meristematic cultures from apical or axillary meristems of sugar beet or other dicotyledonous species on sucrose containing medium. The cytokinin-like growth regulator may be present in the SMM at a concentration as low as about 2.0 mg/L, or about 1.0 mg/L, or about 0.05 mg/L or about 0.01 mg/L, or even lower; alternatively, the cytokinin-like growth regulators may be present in the SMM at a concentration as high as about 5 mg/L, or about 8 mg/L, or 10 mg/L, or about 25, or about 100 mg/L, or even higher. In one embodiment, the cytokinin-like growth regulator is present in the SMM in from about 0.05 mg/L to about 25 mg/L, more preferably from 0.1 mg/L to 10 mg/L, and most preferably from about 0.5 mg/L to about 8 mg/L. Additional growth regulators may be added to the SMM to induce shoot meristematic cultures. Such growth regulators include (gibberellic acid (GA), and those with auxin-like function such as indole-3-acetic acid (IAA), α-naphthaleneacetic acid (NAA), thidiazuron (TDZ), 3,6-dichloro-o-anisic acid (DICAMBA), 2,4,5,-trichlorophenoxyacetic acid (2,4,5-T), 2,4-dichlorophenoxyacetic acid(2,4-D), and other growth regulators known to those skilled in the art.

The multiple shoot cultures that grow on the SMM are cultured under light or dark conditions at a temperature between 15–35° C., preferably cultured under low light intensity (from about 10- to about 30$\mu$ Einsteins) for about 12 to 16 hour day-lengths at a temperature of about 20° C. After about 4 to 6 weeks. The multiple shoot cultures resemble compact rosettes and are ready for transformation.

Multiple shoot cultures may be transformed with any one of many known transformation methods. As used herein, the term "transformation" refers to the stable introduction of a nucleic acid segment generally, a heterologous nucleic acid sequence or gene) into a plant, plant tissue, plant organelle (i.e., a plastid or chloroplast), or plant cell that did not previously contain that gene. Preferably, transformation results in the stable integration of the nucleic acid sequence into the genome of the plant. As used herein, the term "genome" encompasses nuclear genomes, plastid genomes, and mitochondrial genomes.

The inventors of the present invention have also discovered that large amounts of plastids are present in the cells of multiple shoot cultures. Such cultures thus provide an interesting target tissue for plastid transformation.

Accordingly, in an alternative preferred embodiment, a method of the present invention is used to transform the plastid genome of a plant cell. Preferably, the plastid genome of a dicotyledonous plant cell is transformed using a method of the present invention. In another preferred embodiment, the plastid genome of a dicotyledonous plant cell normally recalcitrant to transformation is transformed using a method of the present invention. A major advantage of plastid transformation is that plastids are generally capable of expressing bacterial genes without substantial modification, and plastids are capable of expressing multiple open reading frames under control of a single promoter. Plastid transformation technology is described in U.S. Pat. Nos. 5,451,513; 5,545,817; and 5,545,818; in PCT Application No. WO 95/16783; and in McBride et al., *Proc. Natl. Acad. Sci. USA* 91, 7301–7305 (1994). The basic technique for chloroplast transformation involves introducing regions of cloned plastid DNA flanking a selectable marker together with the gene of interest into a suitable target tissue, e.g., using biolistics or other protoplast transformation method such as calcium chloride or PEG-mediated transformation. The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation. See Z. Svab et al., *Proc. Natl. Acad. Sci. USA* 87, 8526–8530 (1990), and J. M. Staub et al., *Plant Cell* 4, 39–45 (1992). The presence of cloning sites between these markers allowed creation of a plastid targeting vector for introduction of foreign genes. See J. M. Staub, et al., *EMBO J.* 12, 601–606 (1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase. See Z. Svabet al., *Proc. Natl. Acad. Sci. USA* 90, 913–917 (1993). Previously, this marker had been used successfully for high-frequency transformation of the plastid genome of the green alga *Chlamydomonas reinhardtii*. M. Goldschmidt-Clermont, *Nucl. Acids Res.* 19, 4083–4089 (1991). Other selectable markers useful for plastid transformation are known in the art.

Plastid expression, in which genes are inserted by homologous recombination into the several thousand copies of the circular plastid genome present in each plant cell, takes advantage of the enormous copy number advantage over nuclear-expressed genes to permit expression levels that can readily exceed 10% of the total soluble plant protein. In a preferred embodiment of the invention, a nucleotide sequence of interest is inserted into a plastid targeting vector and transformed into the plastid genome of a desired plant host. Plants homoplasmic for plastid genomes containing the nucleotide sequence of interest are preferably obtained, and are preferentially capable of high expression of the nucleotide sequence.

The term "heterologous" is used herein to indicate a nucleic acid sequence (e.g., a gene) or a protein has a different natural origin (i.e., from a different species, or from the same species but in a different chromosomal location, orientation, or copy number) with respect to its current host. "Heterologous" is also used to indicate that one or more of the domains present in a protein differ in their natural origin with respect to other domains present. The term "nucleic acid" as used herein means at least two nucleotides covalently linked together. A nucleic acid of the present invention will generally contain phosphodiester bonds, although in some cases, nucleic acid analogs are included that may have alternate backbones. In addition, mixtures of naturally occurring nucleic acids and analogs and non-naturally occurring nucleic acids and analogs may be used. Nucleic acids may be single stranded or double stranded, as specified, or contain portions of both double stranded or single stranded sequence. The nucleic acid may be DNA, both genomic and cDNA, RNA, or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The transformation method used for a given plant species or specific type of plant tissue depends on the most appropriate method as determined by the skilled artisan, based on known methods. As novel means are developed for the stable insertion of foreign genes into plant cells and for manipulating the modified cells, skilled artisans will be able to select from known means to achieve a desired result. Known transformation techniques useful in the practice of the present invention include, but are not limited to, microparticle bombardment (U.S. Pat. No. 4,945,050 to Sanford et al. and McCabe et al., *Bio/Technology* 6, 923–926); direct DNA uptake (J. Paszkowski et al., *EMBO J.* 3,2717 (1984)); electroporation (M. Fromm et al. *Proc. Natl. Acad. Sci. USA* 82,5824 (1985); microinjection (A. Crossway et al. *Mol. Gen. Genet.* 202, 179 (1986)); and *Agrobacterium*-mediated gene transfer to the plant tissue. In the present invention, microparticle bombardment and *Agrobacterium*-mediated transformation techniques are preferred, with *Agrobacterium*-mediated gene transfer being most preferred.

*Agrobacterium*-mediated gene transfer exploits the natural ability of the bacteria *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes,* respectively, into plant cells. Transformation using *A. rhizogenes* developed analogously to that of *A. tumefaciens.* See U.S. Pat. No. 5,777,200 to Ryals et al., the disclosure of which is incorporated herein by reference in its entirety. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease." The ability to cause disease in the host plant can be removed by deletion of the genes in the T-DNA without loss of DNA transfer and integration. The nucleic acid to be delivered to a plant cell for purposes of transformation (i.e., a heterologous gene) is attached to border sequences that define the end points of an integrated T-DNA.

Any suitable *Agrobacterium* vector or vector system for transforming the plant may be employed according to the present invention. A variety of *Agrobacterium* strains are known in the art and may be used in the methods of the invention. Representative *Agrobacterium* vector systems are described in G. An, et al. *EMBO J.* 4, 277 (1985); L. Herrera-Estrella, et al., *Nature* 303, 209 (1983); L. Herrera-Estrella et al., *EMBO J.* 2, 987 (1983); L. Herrera-Estrella et al., in *Plant Genetic Engineering* (Cambridge University Press, New York, page 63 (1985); Hooykaas, *Plant Mol. Biol.* 13, 327 (1989); Smith et al., *Crop Science* 35, 301

(1995); Chilton, *Proc. Natl. Acad. Sci. USA* 90, 3119 (1993); Mollony et al., *Monograph Theor. Appl. Genet. NY* 19, 148 (1993); Ishida et al., *Nature Biotechnol.* 14, 745 (1996); and Komari et al., *The Plant Journal* 10, 165 (1996), the disclosures of which are incorporated herein by reference in their entirety.

In addition to the T-region of *Agrobacterium*, the Ti (or Ri) plasmid contains a vir region. The vir region is important for efficient transformation, and appears to be species-specific. Binary vector systems have been developed where the manipulated disarmed T-DNA carrying, for example, heterologous DNA and the vir functions are present on separate plasmids. In other words, a heterologous nucleic acid sequence (i.e., gene or genes) of interest and the flanking T-DNA can be carried by a binary vector lacking the vir region. The vir region is then provided on a disarmed Ti-plasmid or on a second binary plasmid. In this manner, a modified T-DNA region comprising heterologous DNA is constructed in a small plasmid which replicates in *E coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. As another alternative, the heterologous nucleic acid sequence and the T-DNA border sequences can be put into the T-DNA site on the Ti-plasmid through a double recombination event by which the new T-DNA replaces the original Ti-plasmid T-DNA. The vir region can be supplied by the Ti-plasmid or on a binary plasmid. As yet a further alternative, the heterologous nucleic acid sequence and flanking T-DNA can be integrated into the bacterial chromosome as described by U.S. Pat. No. 4,940,838 to Schilperoort et al., and the vir region can then be supplied on a Ti-plasmid or on a binary plasmid. Binary vectors as described herein may be used in the practice of the present invention, and are preferred.

Alternatively, in other embodiments of the invention, super-binary or "supervirulent" *Agrobacterium* vectors are employed in the *Agrobacterium* solutions. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (see Japanese Patent Appl. (Kokai) No. 4-222527, European Patent Applications EP 504,869 and EP 604,662, and U.S. Pat. No. 5,591,616, herein incorporated by reference) and pTOK233 (see Komari, *Plant Cell Reports* 9, 303 (1990), and Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also contains an antibiotic resistance gene, a selectable marker gene, and, if desired, a nucleic acid of interest to be transformed into the plant. Super-binary vectors of the invention can be constructed having the features described above for pTOK162. The T-region of the super-binary vectors and other vectors for use in the invention may be constructed to have restriction sites for the insertion of, for example, heterologous genes to be delivered to the plant. Alternatively, heterologous nucleic acids to be transformed can be inserted in the T-DNA region of the vector by utilizing in vivo homologous recombination. See, Herrera-Esterella et al., *EMBO J.* 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Preferably, *Agrobacterium* vectors and vector systems utilized in the methods of the present invention are modified by recombinant nucleic acid techniques to contain a heterologous nucleic acid (e.g., a gene or genes of interest) to be expressed in the transformed cells. "Expression" refers to the transcription and translation of a structural heterologous nucleic acid to yield the encoded protein. Expression may also refer to transcription only, as for example in the case of antisense constructs. The heterologous nucleic acid to be expressed is preferably incorporated into the T-region and is flanked by T-DNA border sequences of the *Agrobacterium* vector.

In addition to coding sequences, the vectors of the present invention may also optionally comprise regulatory sequences useful or necessary for the transcription and translation of the heterologous nucleic acid. Examples of such regulatory sequences include but are not limited to transcriptional initiation regions (including promoters), enhancers, signal sequences, polyadenylation sequences, introns, 5' and 3' noncoding regions (i.e., 5' leader sequences), terminator sequences, and other regulatory elements known to those skilled in the art. General molecular biology techniques that may be used to create the modified vectors used in the invention are well-known by those of skill in the art.

The nucleic acid to be expressed after transformation is preferably placed under the control of a suitable promoter sequence. The term "promoter" refers to the nucleotide sequences at the 5' end of a structural gene or coding sequence that directs the initiation of transcription. As used herein, the term "operatively linked" means that a promoter is connected to a DNA coding region in such a way that the transcription of that DNA coding region is controlled and regulated by that promoter. Means for operatively linking a promoter to a coding region are well known in the art.

For expression in plants, suitable promoters must be chosen for the host cell, the selection of which promoters is well within the skill of one knowledgeable in the art. Promoters useful in the practice of the present invention include, but are not limited to, constitutive, inducible, temporally-regulated, developmentally regulated, chemically regulated, tissue-preferred and tissue-specific promoters.

Numerous promoters are known or are found to facilitate transcription of RNA in plant cells and can be used in the DNA construct of the present invention. Examples of suitable promoters include the nopaline synthase (NOS) and octopine synthase (OCS) promoters, the light-inducible promoter from the small subunit of ribulose bis-phosphate carboxylase promoters, the CaMV 35S and 19S promoters, the full-length transcript promoter from Figwort mosaic virus, histone promoters, tubulin promoters, or the mannopine synthase promoter (MAS). The promoter may also be one that causes preferential expression in a particular tissue, such as leaves, stems, roots, or meristematic tissue, or the promoter may be inducible, such as by light, heat stress, water stress or chemical application or production by the plant. Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters.

Additional promoters useful in the present invention include but are not limited to one of several of the actin genes (e.g., rice actin), which are known to be expressed in most cell types. Yet another constitutive promoter useful in the practice of the present invention is derived from ubiquitin, which is another gene product known to accumulate in many cell types. The ubiquitin promoter has been cloned from several species for use in transgenic plants (e.g., sunflower (Binet et al., *Plant Science* 79: 87–94 (1991)); and maize (Christensen et al., *Plant Molec. Biol.* 12, 619–632 (1989)). Other useful promoters are the U2 and U5 snRNA promoters from maize (Brown et al., *Nucleic Acids Res.* 17, 8991 (1989)) and the promoter from alcohol dehydrogenase (Dennis et al., *Nucleic Acids Res.* 12, 3983 (1984)).

Tissue-specific or tissue-preferential promoters useful in the present invention in plants are those which direct expression in root, pith, leaf or pollen. Such promoters are disclosed in U.S. Pat. No. 5,625,136 (herein incorporated by reference in its entirety). Also useful are promoters which confer seed-specific expression, such as those disclosed by Schernthaner et al., *EMBO J.* 7: 1249 (1988); anther-specific promoters ant32 and ant43D; anther (tapetal) specific promoter B6 (Huffman et al., *J. Cell. Biochem.* 17B, Abstract #D209 (1993)); and pistil-specific promoters such as a modified S13 promoter (Dzelkalns et al., *Plant Cell* 5,855 (1993)).

Other plant promoters may be obtained, preferably from plants or plant viruses, and may be utilized so long as the selected promoter is capable of causing sufficient expression in a plant resulting in the production of an effective amount of the desired protein. In a preferred embodiment of the invention, the promoter is the rice actin-1 promoter.

Any heterologous gene or nucleic acid that is desired to be expressed in a plant is suitable for transformation in the present invention, and can be used in the methods of the invention. Heterologous genes to be transformed and expressed in the plants of the present invention include but are not limited to genes that encode resistance to diseases, genes that encode resistance to insects, genes conferring nutritional value, genes conferring antifungal, antibacterial or antiviral activity, genes conferring resistance to herbicides, genes conferring improved plant or nutritional traits, and the like. Alternatively, therapeutic (e.g., for veterinary or medical uses) or immunogenic (e.g., for vaccination) peptides and proteins can be expressed in plant cells transformed by the methods of the present invention.

The expression of structural genes is preferred. As used herein, a "structural gene" is that portion of a gene comprising a DNA segment encoding a protein, polypeptide or a portion thereof, and excluding the 5' sequence which drives the initiation of transcription. The structural gene may be one which is normally found in the cell or one that is not normally found in the cellular location wherein it is introduced (i.e., is a heterologous gene). A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence, or may include one or more introns, bounded by the appropriate splice junctions. The structural gene may be a composite of segments derived from a plurality of sources, either naturally occurring or synthetic, or both. When synthesizing a gene for improved expression in a host cell it is desirable to design the gene such that its frequency of codon usage approaches the frequency of preferred codon usage of the host cell.

Likewise, the methods of the present invention may be used to transfer any nucleic acid for controlling gene expression a plant. For example, the nucleic acid to be transferred can encode an antisense oligonucleotide. Alternately, plants of the present invention can be transformed with one or more genes to reproduce enzymatic pathways for chemical synthesis or other industrial processes. Heterologous nucleic acids useful in the present invention may be naturally occurring and may be obtained from prokaryotes or eukaryotes (e.g., bacteria, fungi, yeast, viruses, plants, insects, and mammals), or the nucleic acids may be synthesized in whole or in part.

In a preferred embodiment of the invention, the heterologous nucleic acid or gene delivered or transformed into the dicotyledonous multiple shoot culture encodes a polypeptide having protoporphyrinogen oxidase (PPO) activity. See, e.g., U.S. Pat. Nos. 5,767,373; 5,939,602; 6,023,012; and 6,084,155, the disclosures of which are incorporated herein by reference in their entirety. In another preferred embodiment, the nucleic acid or gene delivered or transformed into the dicotyledonous multiple shoot culture encodes a polypeptide having phosphomannose isomerase (PMI) activity. See e.g., U.S. Pat. Nos. 5,767,378 and 5,994,629, incorporated herein by reference in their entirety). In yet another preferred embodiment, the nucleic acid or gene delivered or transformed into the dicotyledonous multiple shoot culture encodes a polypeptide having xylose isomerase (xylA) activity. In still another preferred embodiment, the nucleic acid or gene delivered or transformed into the dicotyledonous multiple shoot culture encodes a polypeptide having GUS activity.

After effecting delivery of heterologous nucleic acid to recipient cells, plastids and/or plants by any of the methods listed above, identifying the cells and plants exhibiting successful or enhanced expression of a heterologous gene for further culturing and plant regeneration generally occurs by one or more screening methods.

"Screening" generally refers to identifying the cells and/ or plants exhibiting expression of a heterologous gene that has been transformed into the plant. Usually, screening is carried out to select successfully transformed seeds (i.e., transgenic seeds) for further cultivation and plant generation (i.e., for the production of transgenic plants). In order to improve the ability to identify transformants, a selectable or screenable marker gene is normally transformed into plant along with the heterologous gene of interest. In such a case, one would then generally assay the potentially transformed cells, seeds or plants by exposing the cells, seeds, plants, or seedlings to a selective agent or agents. For example, transgenic cells, seeds or plants may be screened under selective conditions, such as by growing the seeds or seedlings on media containing selective agents such as mannose or antibiotics (e.g., hygromycin, kanamycin, or paromomycin), the successfully transformed plants having been transformed with genes encoding resistance to such selective agents. Alternatively, other methods (e.g., exposing plants transformed with herbicide-resistant genes to herbicides such as a PPO inhibitor see above or BASTA™) are used to screen the cells, seeds, plants or tissues of the plants for the desired marker gene. Alternatively, a positive selection method with for example a nucleic acid that encodes a polypeptide having phosphomannose isomerase (PMI) activity is used. In a preferred embodiment of the invention, the transformed cells are selected by growing the transformed multiple cultures on plant growth media comprising antibiotics and/or mannose.

In order to improve the ability to identify transformants, one may desire to employ a selectable or screenable marker gene as, or in addition to, the expressible nucleic acid sequence of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Many examples of suitable marker genes are known to the art and can be employed in the practice of the invention. The selectable marker gene may be the only heterologous gene expressed by a transformed cell, or may be expressed in addition to another heterologous gene transformed into and expressed in the transformed cell. Selectable marker genes are utilized for the identification and selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades and detoxifies the herbicide in the plant before it can act. See, DeBlock et al., EMBO J. 6, 2513 (1987); DeBlock et al., Plant Physiol. 91, 691 (1989); Fromm et al., Bio Technology 8, 833 (1990); Gordon-Kamm et al., Plant Cell 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

Selectable marker genes include, but are not limited to, genes encoding: neomycin phosphotransferase II (Fraley et al., CRC Critical Reviews in Plant Science 4, 1 (1986)); cyanamide hydratase (Maier-Greiner et al., Proc. Natl. Acad. Sci. USA 88, 4250 (1991)); aspartate kinase; dihydrodipicolinate synthase (Perl et al., BioTechnology 11, 715 (1993)); bar gene (Toki et al., Plant Physiol. 100, 1503 (1992); Meagher et al., Crop Sci. 36, 1367 (1996)); tryptophane decarboxylase (Goddijn et al., Plant Mol. Biol. 22, 907 (1993)); neomycin phosphotransferase (NEO; Southern et al., J. Mol. Appl. Gen. 1, 327 (1982)); hygromycin phosphotransferase (HPT or HYG; Shimizu et al., Mol. Cell. Biol. 6, 1074 (1986)); dihydrofolate reductase (DHFR); phosphinothricin acetyltransferase (DeBlock et al., EMBO J. 6, 2513 (1987)); 2,2-dichloropropionic acid dehalogenase (Buchanan-Wollatron et al., J. Cell. Biochem. 13D, 330 (1989)); acetohydroxyacid synthase (U.S. Pat. No. 4,761, 373 to Anderson et al.; Haughn et al., Mol. Gen. Genet. 221, 266 (1988)); 5-enolpyruvyl-shikimate-phosphate synthase (aroA; Comai et al., Nature 317, 741 (1985)); haloarylnitrilase (WO 87/04181 to Stalker et al.); acetyl-coenzyme A carboxylase (Parker et al., Plant Physiol. 92, 1220 (1990)); dihydropteroate synthase (sulI; Guerineau et al., Plant Mol. Biol. 15, 127 (1990)); and 32 kDa photosystem II polypeptide (psbA; Hirschberg et al., Science 222, 1346 (1983)).

Also included are genes encoding resistance to chloramphenicol (Herrera-Estrella et al., EMBO J. 2, 987 (1983)); methotrexate (Herrera-Estrella et al., Nature 303, 209 (1983); Meijer et al., Plant Mol. Biol. 16, 807 (1991)); hygromycin (Waldron et al., Plant Mol. Biol. 5, 103 (1985); Zhijian et al., Plant Science 108, 219 (1995); Meijer et al., Plant Mol. Bio. 16, 807 (1991)); streptomycin (Jones et al., Mol. Gen. Genet. 210, 86 (1987)); spectinomycin (Bretagne-Sagnard et al., Transgenic Res. 5, 131 (1996)); bleomycin (Hille et al., Plant Mol. Biol. 7, 171 (1986)); sulfonamide (Guerineau et al., Plant Mol. Bio. 15, 127 (1990); bromoxynil (Stalker et al., Science 242, 419 (1988)); 2,4-D (Streber et al., Bio/Technology 7, 811 (1989)); phosphinothricin (DeBlock et al., EMBO J. 6, 2513 (1987)); spectinomycin (Bretagne-Sagnard and Chupeau, Transgenic Research 5, 131 (1996)).

The foregoing list of selectable marker genes is not meant to be limiting. Any selectable marker gene can be used in the present invention.

To additionally confirm the presence of the heterologous nucleic acid or "transgene(s)" in the seeds of the transformed plant or in the regenerated plants produced from those seeds, a variety of assays may be performed. Such assays include, for example, molecular biological assays, such as Southern and Northern blotting and PCR; biochemical assays, such as detecting the presence of a protein product, by immunological means (ELISAs and Western blots) or by enzymatic function; and by plant part assays, such as leaf or root assays.

While Southern blotting and PCR may be used to detect the gene(s) in question, they do not provide information as to whether the gene is being expressed. Expression of the heterologous gene may be evaluated by specifically identifying the protein products of the introduced genes or evaluating the phenotypic changes brought about by their expression. Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these techniques are among the most commonly employed, other procedures are known in the art and may be additionally used.

One particular advantage of the present invention is that the use of a multiple shoot culture or explant for transformation, rather than a single-shoot culture, increases the efficiency of transformation of plants that are otherwise recalcitrant to transformation. By efficiency is meant the percentage of plants or plant cells successfully transformed with a desired heterologous nucleic acid, as compared to the percentage of plants or plant cells not successfully transformed with the heterologous nucleic acid. In a preferred embodiment of the invention, the transformation efficiency of the method of the invention is higher than about 1%, more preferably higher than 4%, even more preferably higher than 10%, and most preferably higher than about 30%. The transformation efficiency is defined as the ratio between the number of explants giving a transgenic plant and the number of target explants.

Transgenic plants comprising the heterologous nucleic acid of the present invention (e.g., comprising a heterologous nucleic acid of the present invention, or a transformed cell of the present invention), as well as the seeds and progeny produced by the transgenic plants are also an aspect of the present invention. Procedures for cultivating transformed cells to useful cultivars are known to those skilled in the art. Techniques are known for the in vitro culture of plant tissue, and in a number of cases, for regeneration into whole plants. A further aspect of the invention is transgenic plant tissue, plants or seeds containing the nucleic acids described above. In a preferred embodiment, transformed explants produced using the present invention are not chimeric, or only a small proportion of transformed explants is chimeric. This is preferably achieved by extending the period of high cytokinin treatment or by increasing the stringency of mannose selection, or both. (See Example 5, below).

Thus, the transformed cells of the present invention, identified by selection or screening and cultured in an appropriate medium that supports regeneration as provided herein, may then be allowed to mature into plants. Plants are preferably matured either in a growth chamber or greenhouse. Plants are regenerated from about six weeks to ten months after a transformant is identified, depending on the initial tissue. During regeneration, cells may be grown on solid media in tissue culture vessels. Illustrative embodiments of such vessels are petri dishes and Plant Con®s. After the regenerating plants have reached the stage of shoot and root development, they may be transferred to a greenhouse for further growth and testing. As provided above, seeds and progeny plants of the regenerated plants are an aspect of the present invention. Accordingly, the term "seeds" is meant to encompass seeds of the transformed plant, as well as seeds produced from the progeny of the transformed plants. Plants of the present invention include not only the transformed and regenerated plants, but also progeny of transformed and regenerated plants produced by the present invention.

In one embodiment, regenerated transgenic plants of the present invention are made by first growing transformed multiple shoot cultures on selection media and removing all non-transformed tissue as the transformed culture matures. After selection is completed, the shoots produced by the transformed cultures are transferred to containers that preferably contain a shoot elongation medium; such media are known in the art and described below.

If desired, transformed shoots may be cloned on MS-based cloning medium (for example, a growth medium as described above, further comprising mannose). Alternatively, a single shoot or clone may be successfully rooted by transferring the shoot or clone to an appropriate rooting medium as described below or as may be determined by the skilled artisan.

Plants produced by the methods of the present invention may be screened for successful transformation by standard methods described above. Seeds and progeny plants of regenerated plants of the present invention may be continuously screened and selected for the continued presence of the transgenic and integrated nucleic acid sequence in order to develop improved plant and seed lines, which are an another aspect of the present invention. Desirable transgenic nucleic acid sequences may thus be moved (i.e., introgressed or inbred) into other genetic lines such as certain elite or commercially valuable lines or varieties. Methods of introgressing desirable nucleic acid sequences into genetic plant lines may be carried out by a variety of techniques known in the art, including by classical breeding, protoplast fusion, nuclear transfer and chromosome transfer. Breeding approaches and techniques are known in the art, and are set forth in, for example, J. R. Welsh, *Fundamentals of Plant Genetics and Breeding* (John Wiley and Sons, New York, (1981)); *Crop Breeding* (D. R. Wood, ed., American Society of Agronomy, Madison, Wis., (1983)); O. Mayo, *The Theory of Plant Breeding, Second Edition* (Clarendon Press, Oxford, England (1987)); and Wricke and Weber, *Quantitative Genetics and Selection Plant Breeding* (Walter de Gruyter and Co., Berlin (1986)). Using these and other techniques in the art, transgenic plants and inbred lines obtained according to the present invention may be used to produce commercially valuable hybrid plants and crops (e.g., hybrid squash and sugarbeets), which hybrids are also an aspect of the present invention.

The following Examples are provided to illustrate the present invention, and should not be construed as limiting thereof.

EXAMPLE 1

Transformation of Squash

Seed Sterilization and Germination

Mature embryos of squash (*Cucurbita pepo.* L.) are carefully removed from dry seeds using a pair of pliers. They are then placed in 50-ml disposable centrifuge tubes and surface-sterilized in 15% Clorox® solution (V/V) for 15 min. During sterilization, the tubes are placed on a rotator and agitated at 200 rpm. After rinsing three times with sterile water, the embryos are soaked in sterile water for an additional 20 min. The tubes are shaken by hand from time to time to remove the membrane that encloses the embryos. After sterilization, mature embryos are germinated on a MS-based (Murashige and Skoog, 1962) medium supplemented with 4.0 mg/L-BA and grown in a culture room at 23–26° C. in darkness.

Preparation of Explants

Cotyledonary petioles. Three days after germination, the hypocotyls and two-thirds of the cotyledons are removed from the germinating seedlings. The cotyledonary petiole explants, which contain the cotyledonary nodes, shoot tips and the remaining of the cotyledons, are then transferred to a shoot multiplication (SM) medium and grown at 25° C. under light. The SM medium contains MS salts, B5 vitamins, 2–4 mg/L BA- and is solidified with about 4 g/L (or about 0.4% w/v) Phytagel™.

Three to ten days after cultivation on the SM medium, excessive tissues of the elongated hypocotyls and cotyledons are carefully removed and the cotyledonary petioles used for transformation are separated from the shoot tip region. The cotyledonary petioles can also be further cultured on the SM medium for an additional three to fourteen days before use in transformation.

Shoot Tips. The apical or axillary meristems containing shoot primodia, leaf primodia, young leaves and a portion of hypocotyls are excised from germinating seedlings or plantlets. They are maintained on SM medium, grown under light at 25° C. and sub-cultured biweekly. The shoot tip explants are ready for transformation after the first subculture. They can also be used as explants for transformation after several passage of subcultures.

Agrobacterium Strains and Plasmids

Agrobacterium tumefaciens strains such as EHA101, LBA4404, GV3101 and K6 (ATCC# 55964) are used for gene delivery with EHA101 (Hood et al, 1986. J Bacteriology 168: 1291–1301) as the preferred strain. The plasmid used for transformation, pNOV2105, contains the coding sequence for phosphomannose isomerase (PMI), which is driven by a modified Smas gene promoter (Ni et al. (1995) Plant J. 7: 661–676). Smas (mannopine synthase) promoter is derived from Agrobacterium tumefaciens and is enhanced by multiplying the ocs enhancer region. The gene is terminated with the nos 3' region. It also contains an Escherichia coli uidA gene that encodes β-glucuronidase (GUS, Jefferson et al (1986) PROC. NATL. ACAD. SCI. USA 83: 8447–8451). A gus intron (Vancanneyt et al. (1990) Mol. Gen. Genet 220 (2):245–250) has been placed inside the GUS coding sequence. The gene is driven by a Smas promoter and terminated with the nos 3' region. Agrobacteria used for transformation are maintained on a Bacto agar-solidified YP medium (5 g/L yeast extract, 10 g/L peptone and 5 g/L NaCl. pH 6.8) which contains appropriate antibiotics (50 mg/L kanamycin, 100 mg/L spectinomycin, and 100 mg/L carbenicillin). The bacteria are kept at 28° C.

Inoculation and Co-cultivation

Three methods are adopted for inoculating agrobacteria to the explants.

Method 1. Two to three day old A. tumefaciens colonies are collected from the Bacto™ agar-solidified bacteria plates using an inoculating loop. Right before or during inoculating Agrobacteria to the explants, the meristematic region of cotyledon petioles or meristematic cultures of apical and axillary shoot tips are repeatedly surface-wounded either by a surgical blade or a needle. Bacteria inoculation is carried out by applying Agrobacteria on the surface of the target regions prior to wounding, or the Agrobacteria are "pasted" to the blade or the needle prior to the wounding process. Following wounding, a liquid Agrobacterium induction medium (e.g., an AII medium, which comprises SM medium plus 200–600 mg/L acetosyringone, about 1 μl to 6 μl depending on the size of the explants) is immediately applied to the wound area in amount of from about one to about six μL, depending on the size of the explants. Excessive Agrobacteria and AII medium on the surface of the wounded tissue are removed by a sterile filter paper. After being air-dried for a short period of time, the infected explants are transferred to a co-cultivation medium (for example, ACC medium, which comprises AII medium in addition to about 20 g/L sucrose and 30 g/L glucose) and incubated at 22° C. in darkness for two to four days.

Method 2. Two to three day old A. tumefaciens aggregates are collected from YP plates and mixed with 25–50 μl of AII medium. The bacteria are left at room temperature for 30 min before inoculation. Bacterial infection is carried out by applying a small amount of the induced A. tumefaciens mixture to the meristematic region of cotyledon petioles, or to the meristematic cultures from apical and axillary shoot tips prior to wounding. Alternatively, bacterial infection is carried by wounding the target region with a blade or the needle coated with Agrobacterium aggregates. After being air-dried for a short period of time, the infected explants are transferred to ACC co-cultivation medium.

Method 3. A. tumefaciens suspensions used for infection are prepared by either suspending two to three day old bacteria aggregates in AII medium on the day of infection, or by growing the bacteria overnight in YP liquid medium and then re-suspending the bacteria in AII medium prior to infection. In the former case, the suspensions are agitated on a slow motion shaker or shaken gently by hand for 0.5— three hours before use. The final concentration of A. tumefaciens is adjusted to $0.2$–$2.0 \times 10_9$ cfu (colony forming units). For infection, the explants are submerged in the A. tumefaciens suspension and the target regions are wounded either with a blade or with a needle. After infection, excessive liquid on the explants is blotted off with a filter paper and the explants are air-dried for 30 to 60 min until the liquid on the surface cannot be seen. The infected explants are then transferred to ACC medium for co-cultivation.

Shoot Multiplication and Selection

After co-cultivation at ACC medium for two to four days, the infected explants are transferred to a shoot multiplication/selection medium (MSS) and grown at 25° C. under light for two weeks. Subsequent subcultures and selection are carried out at two-week intervals. With each subculture, mannose-resistant green shoot clumps are selected, cut into smaller pieces and transferred to fresh MSS medium. The MSS medium consists of SM medium and antibiotics, either with or without mannose. The concentration of mannose in MSS medium is gradually increased from 0 g/L to 2 g/L, 3 g/l and 4 g/L through the subsequent selection while the concentration of sucrose is decreased from 30 g/L to 25 g/L and then to 20 g/L.

Plant Regeneration

Shoot clumps growing on mannose are maintained and new clones are made on MSS medium that contains two to four g/L mannose and 0.5—four mg/L of 6-benzylaminopurine (BA or 6-BAP). To promote shoot elongation, shoot clumps are grown on MSS medium with or without 0.5 mg/L BA. Shoots are rooted in MSS medium without BA or MSS medium containing 1 mg/L indole-3-butyric acid (IBA). Rooted shoots are transferred to soil and grown to maturity in the greenhouse. Transgenic plants are self-pollinated and/or cross-pollinated with non-transgenic plants to produce T1 progenies. The T1 transgenic progenies are harvested for analysis and are used for producing T2 transgenic progenies.

Plant Analysis

GUS Histochemical Assay. The tissues or organs from transgenic plants and non-transgenic control plants are incubated in a GUS substrate at 37° C. overnight according to the method of Jefferson (Plant Mol. Bio. Rep. 5, 387–405 (1987)). To help visualize GUS expression in leaf tissues, chlorophyll is extracted from the tissues using 70% ethanol, if needed. Transgenic progeny containing the gus gene are screened by performing a GUS histochemical assay on the roots and immature embryos of the progeny. Segregation analysis of the transgene in progeny is performed using a Chi square test.

ELISA Assay. Leaf samples are collected from the transgenic and non-transgenic plants, and an ELISA plus/minus assay is performed to confirm the presence of the PMI enzyme.

Integration of the Transgene. Total DNA is isolated from transgenic plants and non-transgenic control plants. The integration of transgene in the plant genome is confirmed by Southern blot analysis. Results from the transformation with EHA 101 (pNOV2105) are summarized in Table 1.

TABLE 1

| Experiment | No. of Explants | PMI+ and GUS+ | % Expression (GUS+/No. Explants) |
|---|---|---|---|
| 1 | 200 | 2 | 1 |
| 2 | 50 | 1 | 2 |
| 3 | 200 | 3 | 1.5 |
| 5 | 150 | 4 | 2.7 |
| 6 | 200 | 21 | 10.5 |
| 7 | 100 | 4 | 4 |

The transformation efficiency in squash using the multiple shoot transformation approach described in this invention ranged from 1% to 10.5%. Strong GUS activity was observed in the leaves, leaf petioles, roots, stems, shoots, anthers, corolla, calyx, filaments, nectars, pollen grain, stigmas, styles, ovules, epidermis of ovary and immature embryos of the transgenic squash plants. Southern blot analysis confirmed the integration of pmi gene in the genome of the transgenic plants. Inheritance of the transgene (GUS) in the progeny was confirmed by a GUS histochemical assay. Chi square analysis was performed to check the segregation of transgene (GUS) in the progeny. The results showed that the GUS gene segregated at a 3:1 ratio among the progenies (T1's) that were self-pollinated and at a 1:1 ratio among the progenies that were cross-pollinated with non-transgenic plants. Six T2 progenies from 1 self-pollinated T1 plant were selected for further analysis. A total of 136 embryos were collected from those 6 (six) T2 plants and analyzed for the presence of GUS and PMI genes. The results were all positive, confirming the recovery of a homozygous event.

EXAMPLE 2

Transformation of Watermelon

Mature seeds of watermelon (*Citrullus lanatus* (Thumb.) Mansf.) are germinated and multiple shoot cultures are prepared as described in Example 1. The transformation steps and media used for watermelon transformation, including Agrobacteria infection, co-cultivation, selection plant regeneration, are performed as described in Example 1. Results from the transformation with *Agrobacterium tumefaciens* EHA101 harboring pNOV2105 are shown in Table 2. Strong GUS activities were observed in most of the vegetative and reproductive organs and tissues, as described in Example 1. Expression of GUS activities was also observed in the progeny from the self-pollinated transgenic watermelon plants.

TABLE 2

| Experiment | No. of Explants | Transgene | PMI+/GUS+ | % Expression |
|---|---|---|---|---|
| 1 | 50 | uidA | 3 | 6 |

EXAMPLE 3

Transformation of Melon

The seed coat from melon (*Cucumis melo* L) seeds is removed using a pair of forceps and the seeds are sterilized for 1 min. in 70% ethanol followed by 10 min. in 1% hydrochloride. The seeds are rinsed three to four times with sterile water and sowed on a half-strength hormone-free MS medium, at 10 seeds per plate. The seeds are germinated at 22–24° C. for 16 hrs at 3000–4000 lux and for eight hours in darkness. After seven days, the cotyledon and petioles are separated from the seedlings and transferred them to MS30 medium (MS salts, 30 g/L sucrose). One day before transformation, an *A. tumefaciens* culture is started in a universal tube by transferring 50 µl of a stock solution into 5 ml LB medium containing antibiotics. The culture is incubated at 28° C. at 150 rpm for a minimum of 17 hours.

On the day of transformation, 1.2 to 1.5 ml of the overnight-grown Agrobacterium culture is added to the plates containing the cotyledons (final Agrobacterium concentration: $2 \times 10^8$ cfu/ml). Small incisions (wounding) are made in the cotyledon petioles at the site of the meristem. The plates with Agrobacterium+explants are transferred in a vacuum dessicator. Vacuum is applied by a vacuum pump for 1 minute. The vacuum is held for 15 minutes. After 15 minutes the vacuum is released slowly. The Agrobacterium suspension is soaked off the plate. The explants are washed with liquid MS30 by adding MS30 to the plates. The MS30 is soaked from the plates and the explants are dried on sterile filter paper. The explants are placed on BM4.5+0.5 mg/l BAP (BM4.5B), at 20–30 explants per plate. The plates are incubated at 21–23° C. for 16 hours at 1500–2000 lux and then for eight hours of darkness for five days. After five days of co-cultivation, the explants are transferred to a selection medium containing mannose, 0.5 mg/L BA, 0.125 mg/L ancymidol and 1.5 mg/L AgNO$_3$, at ten explants per plate. The plates are placed at 24° C. for 16 hrs at 2000–2500 lux and then placed in darkness for eight hrs, and transferred every two to 2.5 weeks to fresh medium. Shoots of 0.5 mm and larger are transferred to BMM-c medium that contains MS salts, 0.1 mg/l NAA, 3 mg/l AgNO3 and 200 mg/l cefotaxime and 100 mg/l vancomycine. The shoots are transferred every two to three weeks to fresh BMM-c medium.

EXAMPLE 4

Transformation of Sunflower

Sunflower (*Helianthus annuus* L.) seeds are germinated as described in Example 1. Multiple shoot cultures are prepared from the original shoot tip or from the immature inflorescence using the media as described in Example 1. Immature inflorescences are taken from the greenhouse-grown young plants or from in vitro cultured shoot tips. The multiple shoot cultures are transformed with *Agrobacterium tumefaciens* EHA 101 harboring pNOV2105. Strong GUS activity is observed in multiple shoot cultures four weeks after infection. Transgenic plants are recovered following the selection and shoot multiplication steps as described in Example 1. The results are summarized in Table 3.

TABLE 3

| Experiment | No. of Explants | Transgene | PMI+/GUS+ | % Expression |
|---|---|---|---|---|
| 1 | 7 | uidA | 7 | 100 |
| 2 | 10 | uidA | 10 | 100 |

EXAMPLE 5

Transformation of Sugarbeet

Seed Sterilization and Germination

Seeds of sugarbeet (*Beta vulgaris* L.) are scarified using concentrated sulfuric acid for 10 minutes. After thorough rinsing of the seeds to remove residual sulfuric acid, seeds are soaked overnight in water. Surface sterilization is performed the next day using 20% Clorox® (commercially available) for 15 minutes while shaking. Afterwards, seeds are rinsed 5 times with sterile water, then allowed to air dry for 6 hours prior to plating onto seed germination medium (GM) under aseptic culture. In one example, the GM comprised contains Murashige and Skoog (MS) salts (Sigma Chemicals, St. Louis, Mo.) with about 30 g/L sucrose. $B_5$ vitamins (also obtained from Sigma Chemicals), myo-inositol (100 mg/L), pantothenic acid (1 mg/L) and Phytagel® at 3.6 g/L were also included in the GM, as were plant growth regulators with cytokinin-like function. Cytokinin levels are generally within a typical range of 0.5 mg/L to 5 mg/L, and usually between 1.0 and 2.0 mg/L. For sugar beet seeds, the auxin inhibitor TIBA is also added.

Excision and Initiation of Shoot Meristematic Cultures

Shoot tips of 7–14 day old seedlings are excised and plated onto shoot multiplication medium (SMM). In this case, the SMM comprised Murashige and Skoog salts, 30 g/L sucrose, $B_5$ vitamins and Phytagel 8 g/L. In addition, the SMM contained at least one cytokinin growth regulator such as BA, kinetin, 2-ip or zeatin, generally within a concentration range of about 1 to 10 mg/L and usually within a concentration range of 2–6 mg/L. Additional growth regulators such as GA and those with auxin-like function such as IAA, NAA and 2,4-D were also added.

The shoot tips consisted of both apical and axillary shoot meristematic regions, leaf primordia, 3–4 mm of hypocotyl and the cotyledonary leaves which are cut off to reduce further elongation. Every 7–10 days following plating, target explants were subcultured to fresh SMM after removing any new elongated leaf material. Multiple shoot target explants are typically cultured under low light intensity (10–30 λ Einsteins) for 12 to 16 hour day-lengths at 20° C. After 4 to 6 weeks the multiple shoot cultures resemble compact rosettes and are ready for transformation.

Inoculation and Incubation of Multiple Shoot Culture

*Agrobacterium tumefaciens* mediated transformation is utilized for the transformation of the multiple shoot culture. The *A. tumefaciens* strain EHA101 with plasmid pAD1289 and pNOV2105 (containing the PMI selectable marker gene and the GUS scorable marker gene) is grown on solid culture medium consisting of 5 g/L yeast extract, 10 g/L peptone, 5 g/L NaCl and 15 g/L Bactoagar™ for 2–3 days at 28° C. The plasmid pNOV1508 contains pmi gene, which is driven by the modified SMas promoter and terminated with the nos 3' region. It also contains a double-mutated *Arabidopsis* PPO gene (see U.S. Pat. No. 6,084,155), which is driven by the *Arabidopsis* UBQ3 (intron) promoter (see Norris et al., *Plant Molecular Biology* 21,895–906 (1993)) and terminated with the 35S 3' region. One day prior to transformation the multiple shoot culture is prepared for inoculation by removing any remaining elongated leaf material.

To begin inoculation, single colonies of *A. tumefaciens* are collected together on the original YP culture plate using a sterile loop. For the actual inoculation of each target explant, a sterile scapel blade is dipped into the collected *A. tumefaciens* colonies and used to make cuts in the apical and axillary meristem regions of each target. Immediately following this inoculation step, about 4 to 6 µl of MSMG Induction Medium (MS salts, 2 g/L Glucose, MES, and 200 µM acetosyringone) is applied to the wounded surface of each target in some experiments. An effort is made to cut through the center of as many meristematic zones as possible in order to direct gene delivery to shoot meristem producing cells. Ten to twenty target cultures are typically treated in sequence and then allowed to air dry under sterile conditions in a laminar flow hood for 10 minutes. Following the air drying treatment, treated target explants are moved to MSCC co-cultivation medium (MS salts, B5 vitamins, 2 mg/L BA, 30 g/L sucrose, 200 µM acetosyringone). The treated explants are then incubated on MSCC medium for 2–3 days at 22° C. with continuous dark culture.

Target Culture and Selection

Following inoculation and co-cultivation, the multiple shoot explants are transferred to fresh SMM medium with 2 mg/L BA and appropriate antibiotics for a minimum of two days before applying mannose selection pressure. Transformed tissues are selected on gradually increasing amounts of mannose (2 g/L–20 g/L) and decreasing amounts of sucrose (26 g/L–0 g/L) following transformation. Mannose selection levels are increased in a stepwise manner, from 2 g/L mannose+26 g/L sucrose to 3 g/L mannose+24 g/L sucrose, then 4 g/L mannose+22 g/L sucrose, followed by 5 g/L mannose+20 g/L sucrose and 6 g/L mannose+18 g/L sucrose. The multiple shoot cultures continue to grow in size and are carefully divided at each sub-culturing to promote adequate selection pressure. BA levels are maintained at 2 mg/L for typically 16–20 weeks following transformation to continue shoot meristem multiplication under selection. Following this period, the BA level is reduced to 0.25 mg/L for 4–6 weeks and then eliminated to promote shoot elongation. Areas of surviving transformed tissue are continually removed from dying untransformed sections of the original target explant and surviving sections are again carefully divided to promote stringent selection. Selection and shoot regeneration typically progress over a time period of from 10 to about 30 weeks. As young shoots emerg they are separated and isolated under selection for the most efficient selection of transformed shoots.

Elongation of Transformed Shoots

Once the young shoots reach approximately 0.5–1.5 cm, they are transferred to GA7's containing shoot elongation medium (elongation of developing shoots is enhanced by reduction of cytokinin levels) with or without mannose selection as described above. The shoot elongation medium contains MS salts, $B_5$ vitamins, 30% sucrose and Phytagel™ (7.5 g/l). Low levels of cytokinin are incorporated in the elongation medium, within a typical range of 0.1 to 1.0 mg/l. The optimal cytokinin application for sugar beet is 0.5 mg/L kinetin.

Regeneration of Transformed Plants

Transformed shoots are cloned on MS-based cloning medium plus mannose at 5–20 g/L. Multiple shoots from one original transgenic shoot are sometimes desirable, and for this reason a combination of cytokinin and auxin in the basal MS medium was used to induce cloning. Low levels of both growth regulators typically range from 0.1 mg/L to 0.5 mg/L. For sugar beet, MS salts and 30 g/L sucrose with 0.2 mg/L kinetin, 0.1 mg/L NM, and Phytagel™ 7 g/L is used.

Single shoots or clones are successfully rooted when transferred to a rooting medium containing MS basal medium supplemented with one or two auxins such as IBA or NM at 0.5 mg/L to 5 mg/L. In one example, the rooting medium contains 5 mg/L IBA, 0.5 mg/L NM and about 5–20 g/L mannose. Phytagel™ at 5 g/L was found to be an appropriate gelling agent to support root development.

Transformation Results

High efficiency transformation was achieved in sugar beet using multiple shoot cultures as explants Results from sugar beet multiple shoot cultures transformed with *Agrobacterium tumefaciens* containing pNOV2105 are given in Table 4. GUS expression from the transformed sugar beet plants was detected using a histochemical assay. Expression of the PMI gene was determined using a PMI ELISA+/−assay.

TABLE 4

| Experiment | Number of Explants | GUS+ | GUS+ or PMI+ | % Expression (sum of GUS+ or PMI+/ Number of Explants) |
|---|---|---|---|---|
| 1 | 20 | 7 | 10 | 50 |
| 2 | 28 | 16 | 16 | 57 |
| 3 | 31 | 14 | 18 | 58 |
| 4 | 21 | 7 | 7 | 33 |
| 5 | 44 | 7 | 17 | 39 |
| 6 | 41 | 17 | 22 | 54 |
| 7 | 31 | 15 | 15 | 48 |
| 8 | 50 | 20 | 23 | 46 |

In one experiment, where sugar beet multiple shoot cultures were transformed with *Agrobacterium tumefaciens* containing pNOV1508 (a plasmid that contains the PMI selectable marker gene and the mutated *Arabidopsis thaliana* PPO gene), 18 out of 34 explants produced PMI+ plants. Further analysis of those PMI+ transgenic sugar beet plants by Northern analysis showed that 7 of them also expressed the mutated *Arabidopsis thaliana* PPO gene. Those PPO expressing plants were sprayed with a PPO inhibitor herbicide at a field-applicable level and several of them showed dramatically high tolerance to the herbicide. Two transgenic PPO events were selected for T1 seed production. These events were confirmed to be transgenic by PMI ELISA and Southern analysis for the PMI gene. Each was shown to contain multiple copy integrations of the PMI gene. The rooted T0 plants were transferred to soil and grown for 5–6 weeks at greenhouse conditions of 21° C., 60% humidity, 16 hr daylength/8 hr night. After observing normal phenotypic plant development the T0 plants were transferred to vernalization conditions (4° C., 16 hr day/8 hr night) for 16 weeks then acclimated to 14° C. for 2 weeks. Following acclimization the transgenics were returned to greenhouse conditions where normal flower development was observed. The transgenics were self-pollinated and cross-pollinated with non-transgenic plants for seed production. T1 seed was successfully produced, then harvested and sown in soil for germination. T1 seedlings were verified to contain the PMI gene by PMI ELISA analysis. Co-integration of the PMI and PPO transgenes were confirmed by Southern on five T1 plants for each event.

Elimination of Chimeras

Additional steps are taken to reduce the potential of generating transformed plants that are chimeric (partially transgenic). One step is to extend the period of high cytokinin treatment (2 mg/L) to eight to sixteen weeks to continue to stimulate the shoot meristem multiplication culture response under selective pressure. Another step is to increase the stringency of mannose selection (for instance, increase mannose stepwise from 5 g/L to 10 g/L during selection). In one experiment where sugar beet multiple shoot cultures were transformed with EHA101 containing pNOV2105, 35 out of 36 (97%) explants that are analyzed for GUS expression produced completely transgenic shoots (see Table 5 below).

TABLE 5

| | |
|---|---|
| Number of Targets | 45 |
| Initial Selection/Weeks | 5 g/L mannose + 20 g/L sucrose; 2 weeks |
| Subsequent Selection | 6 g/L mannose + 18 g/L sucrose; 2 weeks |
| | 7 g/L mannose + 16 g/L sucrose; 2 weeks |
| | 8 g/L mannose + 14 g/L sucrose; 2 weeks |
| | 10 g/L mannose + 10 g/L sucrose; 4 weeks |
| 2 mg/L BA Treatment | first 8 weeks |
| 0.25 mg/L BA treatment | subsequent 4 weeks |
| Number of targets histochemically assayed (GUS assay) | 36 |
| Number of targets and percentage of targets with fully transgenic shoots (i.e. not chimeric) | 35 (97%) |

EXAMPLE 6

Plastid Transformation Using Meristematic Cultures Derived from Shoot Tips, Leaves or Other Plant Tissues Construction of Sugar Beet Plastid Transformation Vectors The trnV and rps12/7 intergenic region of the *Beta vulgaris* plastid genome is amplified and modified for insertion of chimeric genes. A 1559 bp region (positions 1 to 1560, GenBank accession number AB032426) is PCR amplified from the sugar beet plastid genome and a PstI site is inserted at position 525. A first PCR amplification of 536 bp is performed from total DNA of *B. vulgaris* with the following pair of primers:

Bv16-MluI (5'TTCTT<u>ACGCGT</u>TACTCACCCG 3') having a natural MluI restriction site (underlined), and Bv16S-PstI (5' AAA<u>CTGCAG</u>AAAGAAGTCCCGGCTCCAAGT 3') introducing a PstI site (underlined).

A second PCR amplification of 1049 bp was performed with the following pair of primers:

Bvrps12-BHI (5' AAA<u>GGATCC</u>AAATTGACGGGTTAGTGTG 3') introducing a BamHI restriction site (underlined) and Bvrps12-PstI (5'AAA<u>CTGCAG</u>TCGCACTATTACGGATACGAA 3') introducing a PstI site (underlined). Both PCR reactions are undertaken with Pfu thermostable DNA polymerase in a Perkin Elmer Thermal Cycler 480 according to the manufacturer's recommendations (Perkin Elmer/Roche, Branchburg, N.J.) as follows: 5 min 95° C., followed by 35 cycles 1 min 95° C./1 min 50° C./1 min 72° C., then 10 min at 72° C. The 536 bp amplification product is digested with MluI and PstI to generate a 525 bp MluI/PstI fragment representing the sugar plastid trnV flanking sequence. The 1049 bp amplification product is digested with PstI and BamHI to generate a 1034 bp BamHI/PstI fragment representing the sugar beet rps12/7 flanking sequence.

The tobacco plastid transformation vector pAT238 (PCT WO 00/20612 Novartis, Int pub date Apr. 13, 2000) is cut with MluI and BamHI and the 3.3 kb MluI/BamHI vector fragment was isolated. This fragment is ligated in a three-way reaction with 525 bp MluI/PstI fragment and 1034 bp BamHI/PstI to generate the sugar beet transformation vector pEBcpSBeet backbone. The resulting plasmid comprises a chimeric tobacco::sugarbeet::tobacco plastid trnV and rps12/7 intergenic locus, the 1559 bp sugar beet sequence is flanked by 414 bp tobacco plastid sequence on trnV side and 39 bp on the rps12/7 side. A chimeric aadA gene, which confers resistance to spectinomycin, driven by the tobacco psbA promoter is inserted in the PstI site previously created in the sugar beet sequence. The plasmid clone having the aadA cassette in the orientation towards the rps12/7 flanking region (pEBSB1) is used for subsequent sugar beet multiple shoot transformation.

Sugar Beet Plastid Transformation

Multiple shoot cultures of sugar beet are derived from shoot tips as described in Example 5. The day before bombardment, target explants are cut either into four pieces (cutting from the top to the bottom of the explant) or kept as intact target explants.

On the day of the bombardment, sugar beet target explants (whole or cut pieces) are transferred to SMM media with 12% sucrose. Explants are placed in the center of the target plate to maximize gene delivery. Cut explants are oriented with the cut surfaces facing upwards to maximize gene delivery to the internal cells of the explant. Sterilized particles are coated with the previously described sugar beet plastid transformation vector pEBSB1. DNA-particle preparation is as follows. 60 mg of particles (tungsten or gold) are sterilized with 0.5 ml of 70% ethanol, washed twice with 0.5 ml sterile ddH2O, and then resuspended in 1 ml of 50% glycerol. To a 100 ul aliquot of the particle suspension, 10 ug of DNA, 100 ul of 2.5M CaCl2, 50 ul of 0.1M spermidine is added sequentially and mixed gently with each adding. The DNA coated particles are centrifuged briefly, followed by one wash with 200 ul of 70% ethanol and another wash with 200 ul of 100% ethanol, then resuspended in 100 ul of 100% ethanol. For each of the bombardment, 5 to 10 ul of DNA-particles are used.

Bombardments are carried out with PDS 1000 Helium gun (Bio-Rad, Richmond, Calif.) following a modification of the protocol described by the manufacturer. Plates with the target explants are placed on the third shelf from the bottom of the vacuum chamber, bombarded with 650, 1100, or 1300 p.s.i. rupture disks with single or multiple shots per plate.

After bombardment, the sugar beet explants are placed back in SMM media for 2 days. The sugar beets are then transferred to SMM media with 250 mg/l of spectinomycin for selection. Two weeks later, the tissue is transferred to SMM media containing 500 mg/l of spectinomycin for continuous selection. After one to two months of selection, green spectinomycin-resistant shoots appear on the white tissues and are analyzed.

Tobacco Plastid Transformation

Meristematic cultures are derived from leaf tissues of tobacco, on media containing at least one cytokinin growth regulator such as BAP, in a concentration range of about 0.5 to 5 mg/L, preferably 1 to 2 mg/L. Meristematic cultures are also derived from other parts of tobacco plant. Additional growth regulator(s) such as NAA are also included. In addition to plant regulators, the medium contains MS salts, B5 vitamins, 30 g/L sucrose and 3 g/L agar, with a pH of about 5.8.

The day of bombardment, meristematic cultures are transferred to fresh media, and placed in the center of the plate to maximize gene delivery. Sterilized particles are coated with the tobacco plastid transformation vector pAt238 (see International Application No. PCT WO 00/20612). The DNA-particle preparation and bombardment procedures are similar to the protocols described by manufacturer.

Cultures are transferred to selection media containing 500 mg/L spectinomycin two days after the bombardment. After about 4 weeks of selection, resistant green shoots appear from the white tissues. These primary resistant shoot tissues are subcultured periodically to fresh media containing 500 mg/L spectinomycin.

Three months after selection, 17 independent events from two experiments are analyzed by PCR for aadA gene and the plastid integration. 14 events are confirmed containing aadA and having the plasmid integrated into their plastid genome.

Tomato Plastid Transformation

Various explants from tomato tissue (such as cotyledon, leaf, shoot tips, and the like) are cultured on media containing at least one cytokinin growth regulator (such as zeatin, BAP) to induce meristematic cultures. The cytokinin concentration ranges from about 0.5 to 5 mg/L, preferably from 1 to 2 mg/L. Additional growth regulator(s) such as IAA, NAA are also included. In addition to plant regulators, the medium contains MS salts, B5 vitamins, 30 g/L sucrose and 7.5 g/L Phytagar, pH5.8.

The day of bombardment, meristematic cultures are transferred to fresh media, and placed in the center of the plate to maximize gene delivery. Sterilized particles are coated with plastid DNA, containing tomato or tobacco homologous sequence flanking the selectable marker gene (and the gene of interest). The DNA-particle preparation and bombardment procedures are similar to the protocols described by manufacturer.

Two days after bombardment, cultures are transferred to the selection media containing 500 mg/L spectinomycin. After several weeks of the selection, resistant green shoots will appear from the white tissues. The shoots obtained continue to grow on spectinomycin selection media and contain transformed plastids.

The foregoing is illustrative of the present invention and is not to be construed as limiting thereof. The invention is defined by the following claims, with equivalents of the claims to be included therein.

What is claimed is:

1. A method of producing a transformed dicotyledonous plant, comprising:
   (a) culturing a dicotyledonous plant tissue comprising a meristematic region on a shoot multiplication (SM) medium to produce a multiple shoot culture from the tissue;
   (b) introducing a nucleic acid into a cell of the multiple shoot culture using *Agrobacterium* or microprojectile bombardment, thereby producing a transformed cell comprising the nucleic acid; and
   (c) regenerating a transformed plant from the transformed cell;
   wherein said dicotyledonous plant tissue is squash, melon, watermelon, sunflower, or sugarbeet tissue.

2. The method of claim 1, wherein regenerating comprises:
   selecting a multiple shoot culture comprising a transformed cell;
   growing the multiple shoot culture under conditions that promote shoot elongation to produce at least one transformed shoot; and
   growing the at least one transformed shoot.

3. A transformed multiple shoot culture produced during the method of claim 1.

4. The method of claim 1, wherein said dicotyledonous plant tissue is squash, melon, watermelon, or sunflower tissue comprising either a cotyledonary petiole from a germinating seedling or a shoot tip from a germinating seedling, and said cotyledonary petiole or said shoot tip is cultured on SM medium comprising about 2 to 4 mg/L 6-benzyl-aminopurine (BA).

5. The method of claim 4, wherein said SM medium further comprises MS salts, about 30 g/L sucrose, B5 vitamins, and about 4 g/L Phytagel™.

6. The method of claim 1, wherein said dicotyledonous plant tissue is sugarbeet tissue comprising a shoot tip from a germinating seedling cultured on SM medium comprising about 1 to 10 mg/L of at least one cytokinin growth regulator, and said shoot tip is subcultured to fresh SM medium, after removing any new elongated leaf material, about every 7 to 10 days for about 4 to 6 weeks.

7. The method of claim 6, wherein said cytokinin growth regulator comprises at least one of BA, kinetin, 2-ip, and zeatin.

8. The method of claim 6, wherein said shoot tip comprises apical and axillary shoot meistematic regions, leaf primordia, and a portion of a hypocotyl.

9. The method of claim 6, wherein said SM medium comprises MS salts, about 30 g/L sucrose, B5 vitamins, and about 8 g/L Phytagel™.

10. The method of claim 1, wherein said SM medium further comprises auxin-like growth regulators.

11. The method of claim 1, wherein said nucleic acid is introduced into said cell using *Agrobacterium*.

12. The method of claim 11, wherein a scalpel blade is used to introduce said *Agrobacterium* into at least one of an apical and an axillary meristem region of said multiple shoot culture.

13. The method of claim 12, further comprising applying about 4 to 6 µl of MSMG (MS salts, about 2 g/L glucose, MES, and about 200 µM acetosyringone) to a wounded surface following introduction of said *Agrobacterium*.

14. The method of claim 1, wherein said nucleic acid comprises a nucleic acid that is heterologous to the dicotyledonous plant.

15. The method of claim 2, wherein said dicotyledonous plant tissue is sugarbeet tissue and said conditions that promote shoot elongation comprise culturing on a shoot elongation medium comprising MS salts, B5 vitamins, about 30% sucrose, Phytagel™, and about 0.1 to 1.0 mg/l cytokinin.

16. The method of claim 15, wherein said cytokinin comprises about 0.5 mg/L kinetin.

17. A method of producing a transformed dicotyledonous plant, comprising:

culturing a dicotyledonous plant tissue comprising a meristematic region on a shoot multiplication (SM) medium to produce a multiple shoot culture from said tissue;

using *Agrobacterium* to introduce a nucleic acid into a cell of said multiple shoot culture, thereby producing a transformed cell comprising said nucleic acid; and regenerating a transformed plant from said transformed cell;

wherein said dicotyledonous plant tissue is from a plant of any family selected from Cucurbitaceae, and Chenopodiaceae.

* * * * *